(12) United States Patent
Haasl et al.

(10) Patent No.: US 10,583,301 B2
(45) Date of Patent: Mar. 10, 2020

(54) IMPLANTABLE MEDICAL DEVICE FOR ATRIAL DEPLOYMENT

(71) Applicant: CARDIAC PACEMAKERS, INC., St. Paul, MN (US)

(72) Inventors: Benjamin J. Haasl, Forest Lake, MN (US); Michael J. Kane, St. Paul, MN (US); Arthur J. Foster, Blaine, MN (US); Lance Eric Juffer, Lino Lakes, MN (US); Michael J. Johnson, North Oaks, MN (US); Keith R. Maile, New Brighton, MN (US); Brian L. Schmidt, White Bear Lake, MN (US); Brendan Early Koop, Ham Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 89 days.

(21) Appl. No.: 15/804,768

(22) Filed: Nov. 6, 2017

(65) Prior Publication Data

US 2018/0126179 A1   May 10, 2018

Related U.S. Application Data

(60) Provisional application No. 62/419,176, filed on Nov. 8, 2016.

(51) Int. Cl.
*A61N 1/37* (2006.01)
*A61N 1/375* (2006.01)
(Continued)

(52) U.S. Cl.
CPC ........ *A61N 1/37518* (2017.08); *A61B 5/0422* (2013.01); *A61B 5/686* (2013.01);
(Continued)

(58) Field of Classification Search
CPC .... A61N 1/37518; A61N 1/059; A61N 1/057; A61N 1/3756; A61N 1/37512; A61N 1/365; A61B 5/686; A61B 5/0422
See application file for complete search history.

(56) References Cited

U.S. PATENT DOCUMENTS 3,057,356 A   10/1962   Greatbatch
3,357,434 A   12/1967   Abell
(Continued)

FOREIGN PATENT DOCUMENTS

AU   2008279789 B2   10/2011
AU   2008329620 B2   5/2014
(Continued)

OTHER PUBLICATIONS

US 8,886,318 B2, 11/2014, Jacobson et al. (withdrawn)
(Continued)

*Primary Examiner* — Allen Porter
*Assistant Examiner* — Natasha Patel
(74) *Attorney, Agent, or Firm* — Seager, Tufte & Wickhem LLP.

(57) ABSTRACT

An implantable medical device (IMD) may be deployed within a patient's right atrium at a location near a right atrial appendage of the patient's heart in order to pace the patient's heart and/or to sense electrical activity within the patient's heart. In some cases, an IMD may be implanted within the right atrial appendage. The IMD may include an expandable anchoring mechanism configured to secure the IMD in place.

18 Claims, 22 Drawing Sheets

(51) Int. Cl.
*A61N 1/05* (2006.01)
*A61B 5/042* (2006.01)
*A61B 5/00* (2006.01)
*A61N 1/365* (2006.01)

(52) U.S. Cl.
CPC ............ *A61N 1/057* (2013.01); *A61N 1/059* (2013.01); *A61N 1/365* (2013.01); *A61N 1/3756* (2013.01); *A61N 1/37512* (2017.08)

(56) References Cited

U.S. PATENT DOCUMENTS

| | | |
|---|---|---|
| 3,596,662 A | 8/1971 | Bolduc |
| 3,667,477 A | 6/1972 | Susset et al. |
| 3,713,449 A | 1/1973 | Muller |
| 3,727,616 A | 4/1973 | Lenzkes |
| 3,835,864 A | 9/1974 | Rasor et al. |
| 3,902,501 A | 9/1975 | Citron et al. |
| 3,942,535 A | 3/1976 | Schulman |
| 3,943,936 A | 3/1976 | Rasor et al. |
| 4,010,756 A | 3/1977 | Dumont et al. |
| 4,142,530 A | 3/1979 | Wittkampf |
| 4,151,513 A | 4/1979 | Menken et al. |
| 4,157,720 A | 6/1979 | Greatbatch |
| 4,162,679 A | 7/1979 | Reenstierna |
| 4,198,991 A | 4/1980 | Harris |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,441,210 A | 4/1984 | Hochmair et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,641,664 A | 2/1987 | Botvidsson |
| 4,644,957 A | 2/1987 | Ricciardelli et al. |
| 4,674,508 A | 6/1987 | DeCote |
| 4,681,111 A | 7/1987 | Silvian |
| 4,712,554 A | 12/1987 | Garson |
| 4,721,118 A | 1/1988 | Harris |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,830,006 A | 5/1989 | Haluska et al. |
| 4,858,610 A | 8/1989 | Callaghan et al. |
| 4,860,750 A | 8/1989 | Frey et al. |
| 4,886,064 A | 12/1989 | Strandberg |
| 4,887,609 A | 12/1989 | Cole |
| 4,928,688 A | 5/1990 | Mower |
| 4,953,564 A | 9/1990 | Berthelsen |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,139,033 A | 8/1992 | Everett et al. |
| 5,143,090 A | 9/1992 | Dutcher et al. |
| 5,144,950 A | 9/1992 | Stoop et al. |
| 5,170,784 A | 12/1992 | Ramon et al. |
| 5,170,802 A | 12/1992 | Mehra |
| 5,178,149 A | 1/1993 | Imburgia et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,234,437 A | 8/1993 | Sepetka |
| 5,241,961 A | 9/1993 | Henry |
| 5,243,977 A | 9/1993 | Trabucco et al. |
| 5,250,071 A | 10/1993 | Palermo |
| 5,255,693 A | 10/1993 | Dutcher et al. |
| 5,258,000 A | 11/1993 | Gianturco |
| 5,259,387 A | 11/1993 | DePinto |
| 5,261,916 A | 11/1993 | Engelson |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,304,195 A | 4/1994 | Twyford et al. |
| 5,305,760 A | 4/1994 | McKown et al. |
| 5,312,415 A | 5/1994 | Palermo |
| 5,312,439 A | 5/1994 | Loeb |
| 5,313,953 A | 5/1994 | Yomtov et al. |
| 5,314,458 A | 5/1994 | Najafi et al. |
| 5,314,459 A | 5/1994 | Swanson et al. |
| 5,318,597 A | 6/1994 | Hauck et al. |
| 5,324,316 A | 6/1994 | Schulman et al. |
| 5,324,325 A | 6/1994 | Moaddeb |
| 5,331,966 A | 7/1994 | Bennett et al. |
| 5,334,222 A | 8/1994 | Salo et al. |
| 5,336,252 A | 8/1994 | Cohen |
| 5,342,408 A | 8/1994 | deCoriolis et al. |
| 5,350,397 A | 9/1994 | Palermo et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,383,924 A | 1/1995 | Brehier |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,411,537 A | 5/1995 | Munshi et al. |
| 5,447,533 A | 9/1995 | Vachon et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,487,760 A | 1/1996 | Villafana |
| 5,522,866 A | 6/1996 | Fernald |
| 5,531,780 A | 7/1996 | Vachon |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,571,148 A | 11/1996 | Loeb et al. |
| 5,591,214 A | 1/1997 | Lu |
| 5,620,466 A | 4/1997 | Haefner et al. |
| 5,622,168 A | 4/1997 | Keusch et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |

(56) References Cited

U.S. PATENT DOCUMENTS

| | | |
|---|---|---|
| 5,720,770 A | 2/1998 | Nappholz et al. |
| 5,728,154 A | 3/1998 | Crossett et al. |
| 5,735,887 A | 4/1998 | Barreras, Sr. et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,755,764 A | 5/1998 | Schroeppel |
| 5,759,199 A | 6/1998 | Snell et al. |
| 5,772,693 A | 6/1998 | Brownlee |
| 5,774,501 A | 6/1998 | Halpern et al. |
| 5,779,715 A | 7/1998 | Tu |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,800,535 A | 9/1998 | Howard, III |
| 5,814,089 A | 9/1998 | Stokes et al. |
| 5,827,216 A | 10/1998 | Igo et al. |
| 5,833,715 A | 11/1998 | Vachon et al. |
| 5,836,985 A | 11/1998 | Rostami et al. |
| 5,836,987 A | 11/1998 | Baumann et al. |
| 5,842,977 A | 12/1998 | Lesho et al. |
| 5,851,227 A | 12/1998 | Spehr |
| 5,855,593 A | 1/1999 | Olson et al. |
| 5,865,791 A | 2/1999 | Whayne et al. |
| 5,871,532 A | 2/1999 | Schroeppel |
| 5,873,894 A | 2/1999 | Vandegriff et al. |
| 5,876,429 A | 3/1999 | Schroeppel |
| 5,876,431 A | 3/1999 | Spehr et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,035,239 A | 3/2000 | Patag et al. |
| 6,041,250 A | 3/2000 | DePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,123,724 A | 9/2000 | Denker |
| 6,128,526 A | 10/2000 | Stadler et al. |
| 6,132,456 A | 10/2000 | Sommer et al. |
| 6,141,581 A | 10/2000 | Olson et al. |
| 6,141,588 A | 10/2000 | Cox et al. |
| 6,141,591 A | 10/2000 | Lenarz et al. |
| 6,141,592 A | 10/2000 | Pauly |
| 6,144,879 A | 11/2000 | Gray |
| 6,152,144 A | 11/2000 | Lesh et al. |
| 6,162,195 A | 12/2000 | Igo et al. |
| 6,164,284 A | 12/2000 | Schulman et al. |
| 6,167,310 A | 12/2000 | Grevious |
| 6,200,303 B1 | 3/2001 | Verrier et al. |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,223,079 B1 | 4/2001 | Bakels et al. |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,363,938 B2 | 4/2002 | Saadat et al. |
| 6,368,284 B1 | 4/2002 | Bardy |
| 6,370,434 B1 | 4/2002 | Zhang et al. |
| 6,371,922 B1 | 4/2002 | Baumann et al. |
| 6,381,495 B1 | 4/2002 | Jenkins |
| 6,385,472 B1 | 5/2002 | Hall et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,501,983 B1 | 12/2002 | Natarajan et al. |
| 6,507,755 B1 | 1/2003 | Gozani et al. |
| 6,507,759 B1 | 1/2003 | Prutchi et al. |
| 6,510,345 B1 | 1/2003 | Van et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,556,874 B2 | 4/2003 | Audoglio |
| 6,561,975 B1 | 5/2003 | Pool et al. |
| 6,564,807 B1 | 5/2003 | Schulman et al. |
| 6,574,506 B2 | 6/2003 | Kramer et al. |
| 6,582,441 B1 | 6/2003 | He et al. |
| 6,584,351 B1 | 6/2003 | Ekwall |
| 6,584,352 B2 | 6/2003 | Combs et al. |
| 6,589,230 B2 | 7/2003 | Gia et al. |

(56) References Cited

U.S. PATENT DOCUMENTS

| | | |
|---|---|---|
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,652,555 B1 | 11/2003 | VanTassel et al. |
| 6,656,175 B2 | 12/2003 | Francischelli et al. |
| 6,666,844 B1 | 12/2003 | Igo et al. |
| 6,689,117 B2 | 2/2004 | Sweeney et al. |
| 6,689,150 B1 | 2/2004 | VanTassel et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,783,499 B2 | 8/2004 | Schwartz |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,895,265 B2 | 5/2005 | Silver |
| 6,895,280 B2 | 5/2005 | Meadows et al. |
| 6,897,788 B2 | 5/2005 | Khair et al. |
| 6,904,315 B2 | 6/2005 | Panken et al. |
| 6,907,285 B2 | 6/2005 | Denker et al. |
| 6,917,833 B2 | 7/2005 | Denker et al. |
| 6,922,592 B2 | 7/2005 | Thompson et al. |
| 6,931,282 B2 | 8/2005 | Esler |
| 6,934,585 B1 | 8/2005 | Schloss et al. |
| 6,949,113 B2 | 9/2005 | VanTassel et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,076,305 B2 | 7/2006 | Imran et al. |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,783 B2 | 4/2007 | Fellows et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,231,260 B2 | 6/2007 | Wallace et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,346,391 B1 * | 3/2008 | Osorio .............. A61B 5/0476 600/378 |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,522,962 B1 | 4/2009 | Doron et al. |
| 7,526,342 B2 | 4/2009 | Chin et al. |
| 7,529,589 B2 | 5/2009 | Williams et al. |
| 7,532,932 B2 | 5/2009 | Denker et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,566,336 B2 | 7/2009 | Corcoran et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,615,010 B1 | 11/2009 | Najafi et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |

(56) References Cited

U.S. PATENT DOCUMENTS

| | | |
|---|---|---|
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,904 B2 | 2/2011 | Cowan et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,080,032 B2 | 12/2011 | van der Burg et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,323,309 B2 | 12/2012 | Khairkhahan et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |

(56) References Cited

U.S. PATENT DOCUMENTS

| | | |
|---|---|---|
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,663,273 B2 | 3/2014 | Khairkhahan et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,758,389 B2 | 6/2014 | Glimsdale |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,845,711 B2 | 9/2014 | Miles et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,089,414 B2 | 7/2015 | Zimmerman et al. |
| 9,155,882 B2 | 10/2015 | Grubac et al. |
| 9,161,758 B2 | 10/2015 | Figulla et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |

(56) References Cited

U.S. PATENT DOCUMENTS

| | | | |
|---|---|---|---|
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 2001/0018547 A1 | 8/2001 | Mechlenburg et al. |
| 2002/0026228 A1 | 2/2002 | Schauerte |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0065543 A1 | 5/2002 | Gomperz et al. |
| 2002/0068958 A1 | 6/2002 | Bardy et al. |
| 2002/0072773 A1 | 6/2002 | Bardy et al. |
| 2002/0077556 A1 | 6/2002 | Schwartz |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0123774 A1 | 9/2002 | Loeb et al. |
| 2002/0123785 A1 | 9/2002 | Zhang et al. |
| 2002/0138009 A1 | 9/2002 | Brockway et al. |
| 2002/0173830 A1 | 11/2002 | Starkweather et al. |
| 2002/0183791 A1 | 12/2002 | Denker et al. |
| 2002/0193846 A1 | 12/2002 | Pool et al. |
| 2002/0198604 A1 | 12/2002 | Schulman et al. |
| 2003/0009203 A1 | 1/2003 | Lebel et al. |
| 2003/0028082 A1 | 2/2003 | Thompson |
| 2003/0036773 A1 | 2/2003 | Whitehurst et al. |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0050681 A1 | 3/2003 | Pianca et al. |
| 2003/0074041 A1 | 4/2003 | Parry et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0109914 A1 | 6/2003 | Westlund et al. |
| 2003/0114908 A1 | 6/2003 | Flach |
| 2003/0144701 A1 | 7/2003 | Mehra et al. |
| 2003/0158584 A1 | 8/2003 | Cates et al. |
| 2003/0181958 A1 | 9/2003 | Dobak |
| 2003/0181959 A1 | 9/2003 | Dobak |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0059392 A1 | 3/2004 | Parramon et al. |
| 2004/0068302 A1 | 4/2004 | Rodgers et al. |
| 2004/0087831 A1 | 5/2004 | Michels et al. |
| 2004/0087938 A1 | 5/2004 | Leckrone et al. |
| 2004/0088035 A1 | 5/2004 | Guenst et al. |
| 2004/0098068 A1 | 5/2004 | Carbunaru et al. |
| 2004/0102830 A1 | 5/2004 | Williams |
| 2004/0103906 A1 | 6/2004 | Schulman et al. |
| 2004/0106954 A1 | 6/2004 | Whitehurst et al. |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1* | 7/2004 | Hauser .................. A61N 1/056 607/36 |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172083 A1 | 9/2004 | Penner |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176822 A1 | 9/2004 | Thompson et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0021108 A1 | 1/2005 | Klosterman et al. |
| 2005/0025797 A1 | 2/2005 | Wang et al. |
| 2005/0043765 A1 | 2/2005 | Williams et al. |
| 2005/0057905 A1 | 3/2005 | He et al. |
| 2005/0061320 A1 | 3/2005 | Lee et al. |
| 2005/0070962 A1 | 3/2005 | Echt et al. |
| 2005/0096702 A1 | 5/2005 | Denker et al. |
| 2005/0102003 A1 | 5/2005 | Grabek et al. |
| 2005/0131511 A1 | 6/2005 | Westlund |
| 2005/0149138 A1 | 7/2005 | Min et al. |
| 2005/0165466 A1 | 7/2005 | Morris et al. |
| 2005/0182456 A1 | 8/2005 | Ziobro et al. |
| 2005/0182465 A1 | 8/2005 | Ness |
| 2005/0203410 A1 | 9/2005 | Jenkins |
| 2005/0251238 A1 | 11/2005 | Wallace et al. |
| 2005/0251240 A1 | 11/2005 | Doan |
| 2005/0261741 A1 | 11/2005 | Libbus et al. |
| 2005/0283208 A1 | 12/2005 | Von Arx et al. |
| 2005/0288727 A1 | 12/2005 | Penner |
| 2005/0288743 A1 | 12/2005 | Ahn et al. |
| 2006/0015097 A1 | 1/2006 | Muller et al. |
| 2006/0020316 A1 | 1/2006 | Martinez et al. |
| 2006/0042830 A1 | 3/2006 | Maghribi et al. |
| 2006/0052829 A1 | 3/2006 | Sun et al. |

(56) References Cited

U.S. PATENT DOCUMENTS

| | | |
|---|---|---|
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0095089 A1 | 5/2006 | Soykan et al. |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136001 A1 | 6/2006 | Ortega et al. |
| 2006/0136004 A1 | 6/2006 | Cowan et al. |
| 2006/0161061 A1 | 7/2006 | Echt et al. |
| 2006/0173504 A1 | 8/2006 | Zhu et al. |
| 2006/0173505 A1 | 8/2006 | Salo et al. |
| 2006/0178719 A1 | 8/2006 | Ideker et al. |
| 2006/0200002 A1 | 9/2006 | Guenst |
| 2006/0206151 A1 | 9/2006 | Lu |
| 2006/0206170 A1 | 9/2006 | Denker et al. |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0247680 A1 | 11/2006 | Amplatz et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0075905 A1 | 4/2007 | Denker et al. |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0106357 A1 | 5/2007 | Denker et al. |
| 2007/0135882 A1 | 6/2007 | Drasler et al. |
| 2007/0135883 A1 | 6/2007 | Drasler et al. |
| 2007/0150009 A1 | 6/2007 | Kveen et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0203556 A1 | 8/2007 | Rutten et al. |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0239248 A1 | 10/2007 | Hastings et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0039904 A1 | 2/2008 | Bulkes et al. |
| 2008/0046040 A1 | 2/2008 | Denker et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0077184 A1 | 3/2008 | Denker et al. |
| 2008/0077188 A1 | 3/2008 | Denker et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0208247 A1* | 8/2008 | Rutten ................ A61M 25/04 606/205 |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2008/0319502 A1 | 12/2008 | Sunagawa et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1* | 8/2009 | Hastings ............ A61N 1/37205 607/33 |
| 2009/0210024 A1 | 8/2009 | M. |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069983 A1 | 3/2010 | Peacock, III et al. |
| 2010/0094367 A1 | 4/2010 | Sen |
| 2010/0100144 A1 | 4/2010 | Shuros et al. |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2010/0314775 A1 | 12/2010 | Schwarzbauer |
| 2011/0022113 A1 | 1/2011 | Zdeblick et al. |
| 2011/0034939 A1 | 2/2011 | Kveen et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |

(56) References Cited

U.S. PATENT DOCUMENTS

| | | |
|---|---|---|
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0213233 A1 | 9/2011 | Stevenson et al. |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1* | 11/2011 | Murray, III ......... A61N 1/0573 607/9 |
| 2011/0270340 A1 | 11/2011 | Pellegrini et al. |
| 2011/0270341 A1 | 11/2011 | Ruben et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1* | 5/2013 | Samade ............... A61N 1/3756 607/3 |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0178889 A1 | 7/2013 | Miles et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197609 A1 | 8/2013 | Moore et al. |
| 2013/0218193 A1 | 8/2013 | Erzberger et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018841 A1 | 1/2014 | Peiffer et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142612 A1 | 5/2014 | Li et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |

(56) References Cited

U.S. PATENT DOCUMENTS

| | | |
|---|---|---|
| 2014/0188157 A1 | 7/2014 | Clark |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222015 A1 | 8/2014 | Keast et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0300704 A1 | 10/2014 | Suwito et al. |
| 2014/0303704 A1 | 10/2014 | Suwito et al. |
| 2014/0309706 A1 | 10/2014 | Jacobson |
| 2014/0343348 A1 | 11/2014 | Kaplan et al. |
| 2014/0371818 A1 | 12/2014 | Bond et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0045868 A1 | 2/2015 | Bonner et al. |
| 2015/0051609 A1 | 2/2015 | Schmidt et al. |
| 2015/0051610 A1* | 2/2015 | Schmidt ............ A61N 1/37205 606/129 |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105729 A1* | 4/2015 | Valeti ............... A61M 25/0074 604/173 |
| 2015/0105836 A1 | 4/2015 | Bonner et al. |
| 2015/0126854 A1 | 5/2015 | Keast et al. |
| 2015/0157861 A1 | 6/2015 | Aghassian |
| 2015/0157866 A1 | 6/2015 | Demmer et al. |
| 2015/0173655 A1 | 6/2015 | Demmer et al. |
| 2015/0190638 A1 | 7/2015 | Smith et al. |
| 2015/0196300 A1 | 7/2015 | Tischler et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335884 A1 | 11/2015 | Khairkhahan et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1166820 A2 | 2/2002 |
| EP | 1702648 A2 | 9/2006 |
| EP | 1809372 A2 | 7/2007 |
| EP | 1812104 A1 | 8/2007 |
| EP | 1835962 A1 | 9/2007 |
| EP | 1904166 B1 | 6/2011 |
| EP | 2471452 A1 | 7/2012 |
| EP | 2433675 B1 | 1/2013 |
| EP | 2441491 B1 | 1/2013 |
| EP | 2452721 B1 | 11/2013 |
| EP | 2662113 A3 | 11/2013 |
| EP | 1948296 B1 | 1/2014 |
| EP | 2760541 B1 | 5/2016 |
| EP | 2833966 B1 | 5/2016 |
| FR | 2559391 A1 | 8/1985 |
| JP | 62254770 A | 11/1987 |
| JP | 02307481 A | 12/1990 |
| JP | 576501 A | 3/1993 |
| JP | 6510459 W | 11/1994 |
| JP | 7016299 A | 1/1995 |
| JP | 9508054 T | 8/1997 |
| JP | 10509901 A | 9/1998 |
| JP | 2000051373 A | 2/2000 |
| JP | 2000502931 A | 3/2000 |
| JP | 2002502640 A | 1/2002 |
| JP | 2002510222 A | 4/2002 |
| JP | 2002514478 A | 5/2002 |
| JP | 2004512105 A | 4/2004 |
| JP | 2004173790 A | 6/2004 |
| JP | 2005508208 A | 3/2005 |
| JP | 2005245215 A | 9/2005 |
| JP | 2008540040 A | 11/2008 |
| JP | 2010509901 A | 3/2010 |
| JP | 5199867 B2 | 2/2013 |
| NZ | 526115 A | 10/2006 |
| NZ | 539770 A | 10/2007 |
| NZ | 539771 A | 10/2007 |
| WO | 9500202 A1 | 1/1995 |
| WO | 9510226 A1 | 4/1995 |
| WO | 9620754 A1 | 7/1996 |
| WO | 9636134 A1 | 11/1996 |
| WO | 9724981 A2 | 7/1997 |
| WO | 9725098 A1 | 7/1997 |
| WO | 9826840 A1 | 6/1998 |
| WO | 9906102 A1 | 2/1999 |
| WO | 9939767 A1 | 8/1999 |
| WO | 9958191 A1 | 11/1999 |

(56) References Cited

FOREIGN PATENT DOCUMENTS

| | | |
|---|---|---|
| WO | 9964104 A1 | 12/1999 |
| WO | 0030534 A1 | 6/2000 |
| WO | 0100114 A1 | 1/2001 |
| WO | 0234330 A2 | 5/2002 |
| WO | 02098282 A2 | 12/2002 |
| WO | 03053491 A2 | 7/2003 |
| WO | 03076010 A1 | 9/2003 |
| WO | 2004002572 A1 | 1/2004 |
| WO | 2004012811 A1 | 2/2004 |
| WO | 2005000206 A3 | 1/2005 |
| WO | 2005042089 A1 | 5/2005 |
| WO | 2005101660 A1 | 10/2005 |
| WO | 2006045073 A1 | 4/2006 |
| WO | 2006045074 A2 | 4/2006 |
| WO | 2006045075 A1 | 4/2006 |
| WO | 2006065394 A1 | 6/2006 |
| WO | 2006086435 A3 | 8/2006 |
| WO | 2006096685 A1 | 9/2006 |
| WO | 2006113659 A1 | 10/2006 |
| WO | 2006124833 A3 | 11/2006 |
| WO | 2007059386 A2 | 5/2007 |
| WO | 2007067231 A1 | 6/2007 |
| WO | 2007067253 A1 | 6/2007 |
| WO | 2007073435 A1 | 6/2007 |
| WO | 2007075974 A2 | 7/2007 |
| WO | 2007078770 A2 | 7/2007 |
| WO | 2007115044 A2 | 10/2007 |
| WO | 2008011626 A1 | 1/2008 |
| WO | 2008034005 A2 | 3/2008 |
| WO | 2008111998 A1 | 9/2008 |
| WO | 2009006531 A1 | 1/2009 |
| WO | 2009099597 A1 | 8/2009 |
| WO | 2012054102 A1 | 4/2012 |
| WO | 2013080038 A2 | 6/2013 |
| WO | 2013098644 A3 | 7/2013 |
| WO | 2013184787 A1 | 12/2013 |
| WO | 2014120769 A1 | 8/2014 |

OTHER PUBLICATIONS

International Search Report and Written Opinion for Application No. PCT/US2017/060221, 26 pages, dated Feb. 9, 2018.
"Instructions for Use System 1, Leadless Cardiac Pacemaker (LCP) and Delivery Catheter," Nanostim Leadless Pacemakers, pp. 1-28, 2013.
Hachisuka et al., "Development and Performance Analysis of an Intra-Body Communication Device," The 12th International Conference on Solid State Sensors, Actuators and Microsystems, vol. 4A1.3, pp. 1722-1725, 2003.
Seyedi et al., "A Survey on Intrabody Communications for Body Area Network Application," IEEE Transactions on Biomedical Engineering,vol. 60(8): 2067-2079, 2013.
Spickler et al., "Totally Self-Contained Intracardiac Pacemaker," Journal of Electrocardiology, vol. 3(384): 324-331, 1970.
Wegmüller, "Intra-Body Communication for Biomedical Sensor Networks," Diss. ETH, No. 17323, 1-173, 2007.

\* cited by examiner

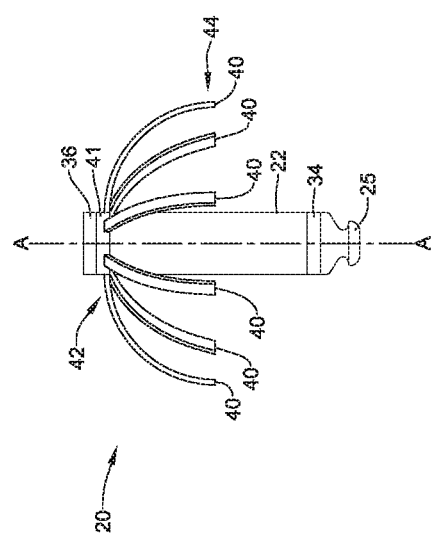

IMPLANTABLE MEDICAL DEVICE FOR ATRIAL DEPLOYMENT

CROSS REFERENCE TO RELATED APPLICATIONS

This application claims the benefit of U.S. Provisional Patent Application Ser. No. 62/419,176 filed on Nov. 8, 2016, the disclosure of which is incorporated herein by reference.

TECHNICAL FIELD

The disclosure relates generally to implantable medical devices, and more particularly to implantable medical devices that can be deployed within or near the patient's heart.

BACKGROUND

Implantable medical devices are commonly used today to monitor a patient and/or deliver therapy to a patient. For example, implantable sensors are often used to monitor one or more physiological parameters of a patient, such as heart beats, heart sounds, ECG, respiration, etc. In some instances, pacing devices are used to treat patients suffering from various heart conditions that may result in a reduced ability of the heart to deliver sufficient amounts of blood to a patient's body. Such heart conditions may lead to slow, rapid, irregular, and/or inefficient heart contractions. To help alleviate some of these conditions, various medical devices (e.g., pacemakers, defibrillators, etc.) can be implanted in a patient's body. Such devices may monitor and in some cases provide electrical stimulation to the heart to help the heart operate in a more normal, efficient and/or safe manner.

SUMMARY

This disclosure provides design, delivery and deployment methods, and clinical usage alternatives for medical devices. In one example, an implantable medical device (IMD) such as a leadless cardiac pacemaker (LCP) may include a power source, circuitry operatively coupled to the power source, a housing at least partially enclosing the circuitry, an anode electrode operatively coupled to the circuitry, a cathode electrode operatively coupled to the circuitry and spaced from the anode electrode, and an expandable anchoring member secured relative to the housing. In some cases, the circuitry may be configured to pace a patient's heart and/or sense electrical activity of the patient's heart. The housing may be positioned within an atrium of the patient's heart. The expandable anchoring member may have a collapsed configuration for delivery and an expanded configuration for securing the housing within the atrium of the patient's heart, sometimes with the cathode electrode in engagement with an atrium wall of the patient.

Alternatively or additionally, the expandable anchoring member may be configured to engage an atrial appendage of the patient's heart in the expanded configuration.

Alternatively or additionally to any of the embodiments above, the expandable anchoring member may include a plurality of struts that extend out from a central hub in the expanded configuration, wherein the housing may be secured to the central hub.

Alternatively or additionally to any of the embodiments above, the expandable anchoring member may extend along a central axis from a first end to a second end, and wherein in the expanded configuration the plurality of struts may extend toward the central axis to the central hub at the first end and out further from the central axis at the second end.

Alternatively or additionally to any of the embodiments above, the plurality of struts may be biased to expand away from the central axis at the second end when transitioning from the collapsed configuration to the expanded configuration.

Alternatively or additionally to any of the embodiments above, the LCP may further include a plurality of fixation features supported by one or more of the plurality of struts facing away from the central axis for engaging the patient's heart and to secure the expandable anchoring member and the housing to the patient's heart.

Alternatively or additionally to any of the embodiments above, the plurality of fixation features may be configured to engage an atrial appendage of the patient's heart as the plurality of struts radially expand from the central axis at the second end of the expandable anchoring member.

Alternatively or additionally to any of the embodiments above, the plurality of struts may be biased to keep the plurality of fixation features engaged with the patient's heart.

Alternatively or additionally to any of the embodiments above, the housing may be removably secured to the expandable anchoring member.

Alternatively or additionally to any of the embodiments above, the power source may be removably coupled relative to the housing, and may be removable relative to the housing while the housing remains secured to the expandable anchoring member.

Alternatively or additionally to any of the embodiments above, the LCP may further include a mesh secured to the expandable anchoring member, wherein the mesh may be configured to encourage endothelialization over at least part of the expandable anchoring member.

Alternatively or additionally to any of the embodiments above, the expandable anchoring member may comprise the cathode electrode and may further comprises an interconnect for providing a connection to the cathode electrode, and wherein the circuitry may be operatively coupled to the interconnect and thus the cathode electrode.

Alternatively or additionally to any of the embodiments above, the expandable anchoring member may comprise a plurality of struts that extend out from a central hub in the expanded configuration, wherein the cathode electrode may be part of or supported by at least one of the plurality of struts.

Alternatively or additionally to any of the embodiments above, the expandable anchoring member comprises a plurality of circumferentially spaced electrodes configured to engage the atrium of the patient's heart, wherein the plurality of circumferentially spaced electrodes may be operatively coupled to the circuitry.

Alternatively or additionally to any of the embodiments above, the circuitry may be configured to utilize one or more of the circumferentially spaced electrodes for sensing electrical signals of the patient's heart and/or to utilize one or more of the circumferentially spaced electrodes for pacing the patient's heart.

In another example of the disclosure, an implantable medical device (IMD) may include a power source, circuitry operatively coupled to the power source, a housing at least partially enclosing the circuitry, an anode electrode operatively coupled to the circuitry, a cathode electrode operatively coupled to the circuitry and spaced from the anode electrode, and an expandable anchoring member secured relative to the housing. The circuitry may be configured to pace a patient's heart and/or sense electrical activity of the patient's heart. The housing may be configured to be positioned within an atrium of the patient's heart. The expandable anchoring member having a collapsed configuration for delivery and an expanded configuration for securing the housing within the atrium of the patient's heart. Further, the expandable anchoring member may extend from a first end to an open second end and may include a plurality of struts connected to a central hub at the first end and extend out to the open second end.

Alternatively or additionally, the housing may be secured to the central hub.

Alternatively or additionally to any of the embodiments above, at least part of the housing may be releasably fixed to the expandable anchoring member.

Alternatively or additionally to any of the embodiments above, the IMD may further include a mesh secured to the expandable anchoring member, wherein the mesh may be configured to encourage endothelialization over at least part of the expandable anchoring member.

In another example of the disclosure, an IMD may include a housing, an anode electrode fixed relative to the housing, a cathode electrode fixed relative to the housing and spaced from the anode electrode, and an expandable anchoring member secured relative to the housing. The housing may be configured to be positioned within an atrium of a patient's heart. The expandable anchoring member may have a collapsed configuration for delivery and an expanded configuration for securing the housing within the atrium of the patient's heart. Further, the expandable anchoring may comprise a plurality of struts that, in the expanded configuration, may assume a cup shape.

The above summary of some illustrative embodiments is not intended to describe each disclosed embodiment or every implementation of the present disclosure. The Figures and Description which follow more particularly exemplify these and other illustrative embodiments.

BRIEF DESCRIPTION OF THE FIGURES

The disclosure may be more completely understood in consideration of the following description in connection with the accompanying drawings, in which:

FIG. 7B is a schematic diagram of the illustrative IMD of FIG. 7A in an expanded configuration;

Figure 1:
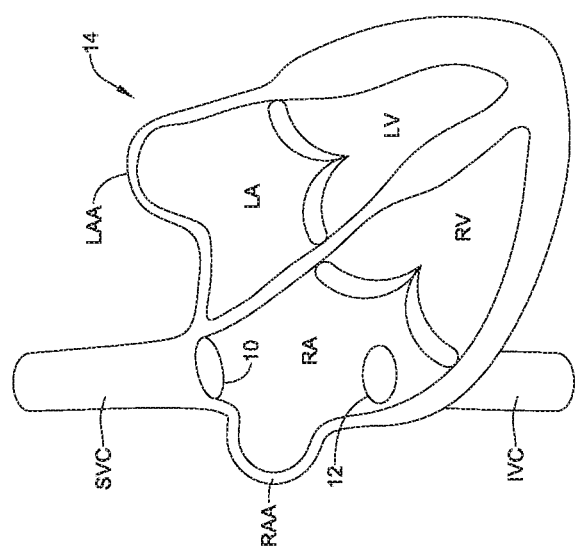
FIG. 1 is a schematic illustration of a human heart.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following description should be read with reference to the drawings in which similar structures in different drawings are numbered the same. The drawings, which are not necessarily to scale, depict illustrative embodiments and are not intended to limit the scope of the disclosure.

FIG. 1 is a schematic illustration of a heart H, illustrating a right atrium RA, a right ventricle RV, a left atrium LA, a left ventricle LV, a right atrial appendage (RAA), and a left atrial appendage (LAA). For simplicity, some of the vasculature around the heart H, such as the aorta, the pulmonary arteries and the pulmonary veins are not shown. However, the superior vena cava (SVC), which returns blood from the upper body to the right atrium RA, and the inferior vena cava (IVC), which returns blood from the lower body to the right atrium RA are shown. The SVC extends to an SVC terminus 10, where the SVC is fluidly coupled with the right atrium RA. The IVC extends to an IVC terminus 12, where the IVC is fluidly coupled with the right atrium RA.

In some cases, one or more of the right atrium RA and the left atrium LA may include an appendage. Such appendages may be considered to be separate from a respective atrium or may be considered to be part of the respective atrium. A right atrial appendage (RAA) and a left atrial appendage (LAA) is shown in FIG. 1.

In some cases, it may be desirable to pace a patient's heart and sense electrical signals by providing pacing and/or sensing in or around the right atrium RA in addition to or as alternative to providing pacing in the right ventricle RV, left atrium LA and/or left ventricle LV. This may be particularly so for DDD pacing (Dual pacing locations (e.g., in the atrium and ventricle), Dual sensing locations (e.g., in the atrium and the ventricle), and Dual modes (e.g., inhibiting mode and triggered mode). The right atrium RA may have a thinner wall and/or less volume than the right ventricle RV, left atrium LA and/or left ventricle LV, such that the same form factors and/or the same fixation mechanisms used in the right ventricle RV, left atrium LA and/or left ventricle LV may not be ideal for use in the right atrium RA.

In some cases, it may be desirable to pace a patient's heart and sense electrical signals by providing pacing and/or sensing in or around the left atrium LA in addition to or as alternative to providing pacing in the right ventricle RV, right atrium RA and/or left ventricle LV. The left atrium LA may have a thinner wall and/or less volume than the right ventricle RV, right atrium RA and/or left ventricle LV, such that the same form factors and/or the same fixation mechanisms used in the right ventricle RV, right atrium RA and/or left ventricle LV may not be ideal for use in the left atrium LA.

An implantable medical device (IMD) may be implanted within the RAA such that the IMD may be able to sense electrical cardiac activity within and/or around the RAA and/or the right atrium RA. In some instances, as will be discussed, an IMD disposed within the RAA may include a lead structure that extends into the right atrium RA or other portion of the heart H. Alternatively or in addition, an implantable medical device (IMD) may be implanted within the LAA such that the IMD may be able to sense electrical cardiac activity within and/or around the LAA and/or the left atrium LA. In some instances, as will be discussed, an IMD disposed within the LAA may include a lead structure that extends into the left atrium RA or other portion of the heart H.

Figure 2A:
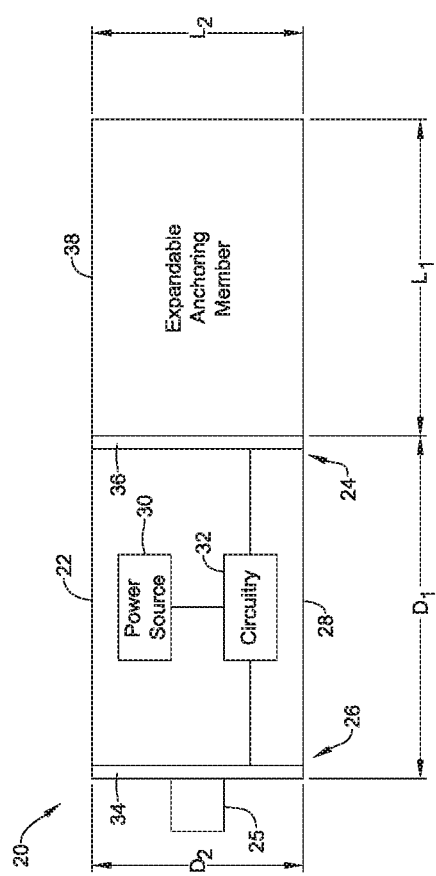
FIGS. 2A and 2B are schematic diagrams of illustrative implantable medical devices (IMD) that have an expandable anchoring member expandable from a collapsed configuration to an expanded configuration.
Figure 2B:
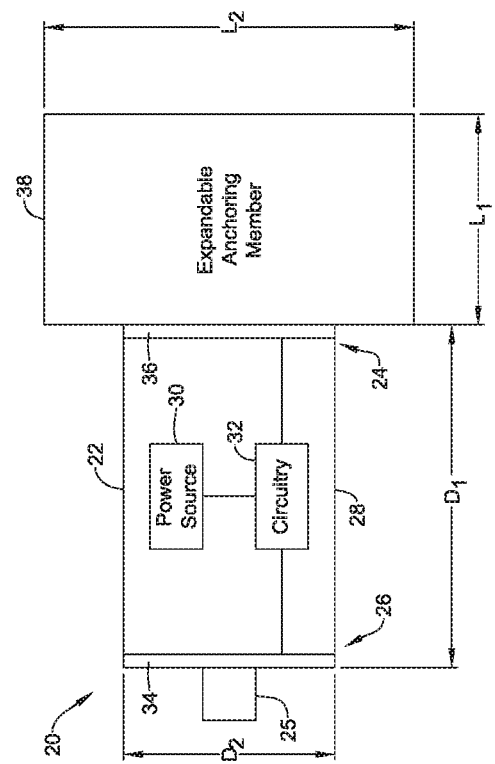

FIGS. 2A and 2B are schematic diagrams of an illustrative IMD 20 that may, for example, be implantable within an atrial appendage (e.g., the RAA or the LAA). The illustrative IMD 20 may include a housing 22. In some cases, the housing 22 may include opposing ends (e.g., a first end 24 and a second end 26), with a side wall 28 extending between the opposing ends 24 and 26. The housing 22 may have a length dimension denoted by a dimension D1 and a width dimension that may be normal to the length direction and that is denoted by a dimension D2. In some cases, D1 may be larger than D2. In some instances, D1 is at least twice D2, or at least three times D2, or in some cases D1 is at least four times D2 or more. In other cases, D2 is larger than D1.

A power source 30 may be disposed within (as shown in FIGS. 2A and 2B) and/or attached to the housing 22. In some cases, the power source 30 may be a battery. In some cases, the power source 30 may be rechargeable, such as a rechargeable battery, a capacitor such as a super-capacitor, and/or any other suitable rechargeable power source.

Circuitry 32 may be disposed at least partially within the housing 22 and may be operably coupled to the power source 30. The circuitry 32 may be operatively coupled to the power source 30, such that the circuitry 32 may draw power from the power source 30. In some cases, the circuitry 32 may be configured to sense the heart H and/or to sense electrical activity of the heart H via one or more electrodes that are exposed outside of the housing 22. Although not shown, the housing may include one or more sensors, such as an ECG sensor, an accelerometer, a gyro, a pressure sensor, a temperature sensor and/or any other suitable sensor. Moreover, in some cases, the circuitry 32 may include communication circuitry for communicating with one or more remotely located devices, such as a leadless cardiac pacemaker (LCP) located elsewhere the heart (e.g. in a ventricle), a subcutaneous implantable cardiac defibrillator (SICD), a remote programmer or any other suitable device.

In the example of FIG. 2A-2B, an anode electrode 34 may be fixed relative to the housing 22. In some cases, a cathode electrode 36 may be fixed relative to the housing 22 and may be spaced apart from the anode electrode 34. The anode electrode 34 may be disposed proximate the first end 24 of the housing 22 while the cathode electrode 36 may be disposed proximate the second end 26 of the housing 22, but this is not required in all cases. In some cases, the cathode electrode 36 may be positioned along the side wall 28 and/or may be positioned in one or more other location configured to allow the cathode electrode 36 to be in engagement with the RAA, right atrium, LAA, or left atrium of a patient's heart when the IMD 20 is implanted. In some cases, the cathode electrode 36 may extend radially outwardly from the housing 22 to facilitate good engagement between the cathode electrode 36 and surrounding tissue. The anode electrode 34 may also be on the side wall 28, or may be at the first end 24 or located elsewhere. The anode electrode 34 and the cathode electrode 36 may each be operably coupled to the circuitry 32 to receive electrical signals from and/or provide electrical signals to the circuitry 32.

The anode electrode 34 and the cathode electrode 36 may be any type of electrode. In one example, one or more of the electrodes may be a ring electrode, a strip electrode, a flexible electrode, a post electrode and/or may assume any other suitable electrode configuration. In some cases, there may be a plurality of cathode electrodes and/or a plurality of anode electrodes. It is contemplated that the plurality of cathode electrodes may be connected in parallel to provide a distributed cathode electrode. Alternatively, it is contemplated that each of the plurality of cathode electrodes may be selectively connectable to the circuitry 32 by a switching circuit, such that the circuitry 32 can use any one (or set) of the plurality of cathode electrodes as the cathode electrode 36 at any given time.

In some cases, the housing 22 may include one or more retrieval features, such as a retrieval feature 25. In one example, the retrieval feature 25 may be located at or near the second end 26 of the housing 22, as shown in FIGS. 2A and 2B. Alternatively, the retrieval feature 25 may be located at or near the first end 24, if desired. In some cases, the housing 22 may include no retrieval features, one retrieval feature, two retrieval features, or more than two retrieval features. The retrieval feature(s) 25, if present, may take any desired shape or configuration. In some cases, the retrieval features 25, if present, may take the form of a knob, clasp, hook, or other feature that can be engaged by a snare or other retrieval device. These are just some examples.

The illustrative IMD 20 of FIGS. 2A-2B may include an expandable anchoring member 38 secured to the housing 22. The housing 22 may be disposed at least partially or entirely within the expandable anchoring member 38 and/or may extend from and/or to an exterior of the expandable anchoring member 38.

The expandable anchoring member 38 may, for example, have a collapsed or delivery configuration (e.g., as shown in FIG. 2A) to facilitate delivery through the vasculature to a location within the heart H (e.g., within the RA, RAA, LA, LAA). The expandable anchoring member 38 may also have an expanded configuration (e.g., as shown in FIG. 2B) that may locate the IMD 20 within the heart H and secure the IMD 20 in place, with the cathode electrode 36 in engagement and/or in electrical communication with one or more walls of the heart H.

The expandable anchoring member 38 may include any radially or otherwise expanding structure configured to secure the IMD 20 at a location within the heart H. In one example, a radially expanding expandable anchoring member 38 radially expand to engage walls of the RAA, LAA and/or other walls of the heart.

As shown in FIGS. 2A and 2B, the illustrative expandable anchoring member 38 may have a first dimension L1 and a second dimension L2, where the second dimension L2 may be substantially perpendicular to the first dimension L1. In a collapsed configuration, as shown in FIG. 2A, the first dimension L1 of the expandable anchoring member 38 may have a first measure and in an expanded configuration, as shown in FIG. 2B, the first dimension L1 may have a second measure that is less than the first measure. Additionally, in a collapsed configuration, as shown in FIG. 2A, the second dimension L2 of the expandable anchoring member 38 may have a first dimension and in an expanded configuration, as shown in FIG. 2B, the second dimension L2 may have a second measure that may be greater than the first measure.

Although not required, in the collapsed configuration, a measure of the first dimension L1 may be greater than a measure of the second dimension L2 and in the expanded configuration a measure of the first dimension L1 may be less than a measure of the second dimension L2. Further, a measure of the dimension L2 may be substantially equal to or less than a measure of dimension D2 of the housing 22 to facilitate delivery of the IMD 20 through vasculature of the patient, such inside of a delivery catheter. In other instances (e.g., optionally when the housing 22 is located within the expandable anchoring member 38 and/or other instances), a measure of dimension L2 may be greater than a measure of dimension D2.

Figure 3A:
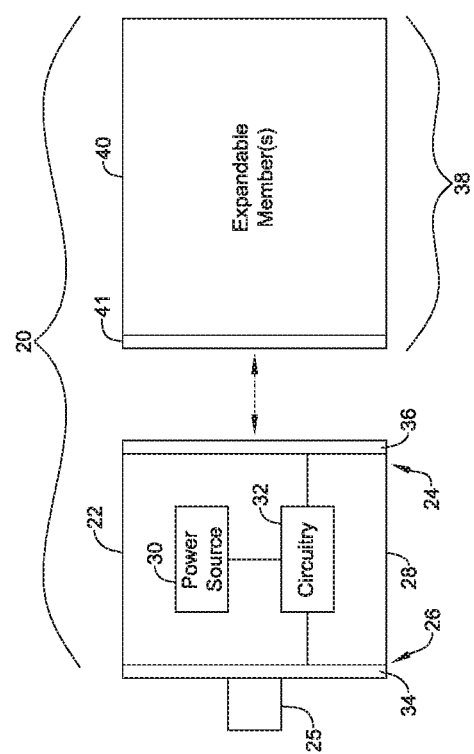
FIGS. 3A and 3B are schematic diagrams of an IMD having a housing separable from an expandable anchoring member.
Figure 3B:
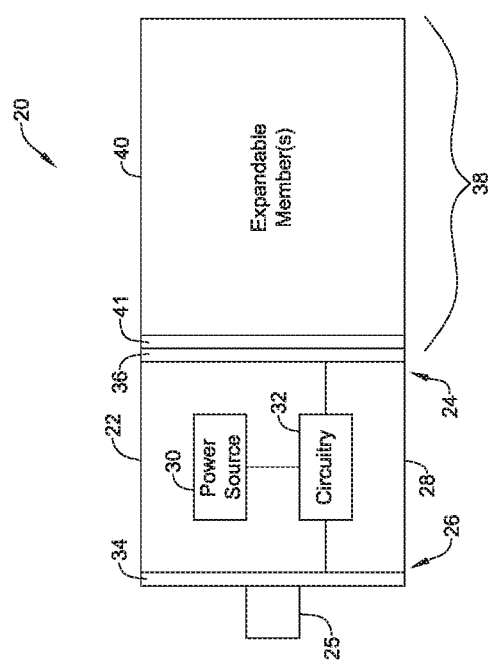

FIGS. 3A and 3B are a schematic representation of an IMD 20 that may have the expandable anchoring member 38 including a hub 41 (e.g., a central hub or other hub). FIG. 3A depicts the housing 22 separated from the hub 41 of the expandable anchoring member 38. FIG. 3B depicts the housing 22 attached to the hub 41 of the expandable anchoring member 38. An ability to detach the housing 22 from the hub 41 of the expandable anchoring member 38 may allow for replacement of the housing 22 and its components to facilitate replacing the housing and/or updating components thereof without having to remove the expandable anchoring member 38 from its implanted location.

In some cases, one or more expandable members 40 of the expandable anchoring member 38 may extend from the hub 41. The hub 41 may include a substantially rigid support from which the expandable members 40 extend. The hub 41 may be formed from the same or different material as the expandable members 40. Further, the hub 41 may be monolithically formed with the expandable members 40 and/or one or more of the expandable members 40 may be affixed to the hub 41. The expandable members 40 may be affixed to the hub 41 in any suitable manner including, but not limited to, welding, brazing, soldering, clasping, and/or using adhesives.

In some cases, the housing 22 may be attached to the expandable anchoring member 38. The attachment may be a permanent attachment or a releasable attachment. A permanent attachment may include a weld attachment, braze attachment, solder attachment, and/or other suitable attachments. A releasable attachment may include a threaded attachment, a ball detent attachment, an actuatable attachment, and/or any other suitable attachment that facilitates separation of the housing 22 from the expandable anchoring member 38 after implantation of the IMD 20.

Figure 4A:
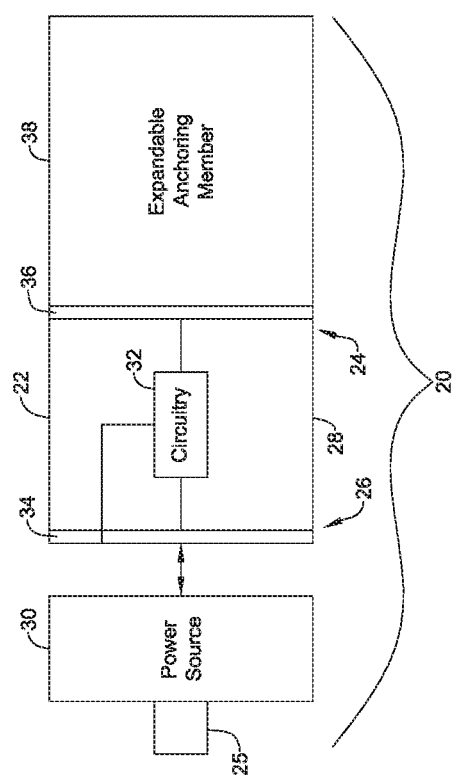
FIGS. 4A and 4B are schematic diagrams of an IMD having a power source separable from a housing and an expandable anchoring member.
Figure 4B:
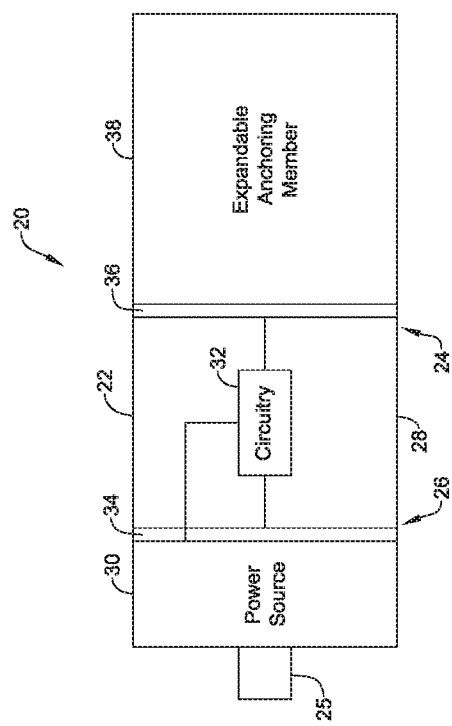

FIGS. 4A and 4B are schematic representations of an IMD 20 with the power source 30 at or adjacent a proximal end of the IMD 20 (e.g., at or adjacent to the second 26 of the housing 22). FIG. 4A depicts the power source 30 and retrieval feature 25 separable from a second end 26 of the housing 22 of the IMD 20. FIG. 4B depicts the power source 30 and retrieval feature 25 attached to the second end 26 of the housing 22. An ability to detach the power source 30 from the housing 22 may allow for replacement of the power source 30 as it depletes over time (e.g., its charge deteriorates or otherwise wears) without having to remove the housing 22 and/or the expandable anchoring member 38.

In some cases, the power source 30 may be removably attached to the housing 22, where the retrieval feature 25 may be a part of or attached to the power source 30. The power source 30 may be attached to the housing 22 through a threaded connection, a ball detent attachment, an actuatable attachment, and/or any other suitable attachment that facilitates separation of the power source 30 from the housing 22 after implantation of the IMD 20. In one example, the retrieval feature 25 may be grasped by a snare or other device and then rotated to disengage threads of the power source 30 from threads of the housing 22. Alternatively, the power source 30 may be fixedly attached to the housing 22.

Further, in addition to the power source 30 being mechanically attached or connected to the housing 22, the power source 30 may be in electrical communication with the circuitry 32 of the IMD 20. The electrical connection between the power source 30 and the circuitry 32 may be made using electrical contacts. In one example, an attachment mechanism for connecting the power source 30 to the housing 22 may be configured to bring two or more electrically conductive surface of the power source 30 into electrical connection with corresponding electrically conductive surfaces of the housing 22, where the electrically connected surfaces of the housing 22 may be in electrical communication with the circuitry 32, but this is not required.

Figure 5:
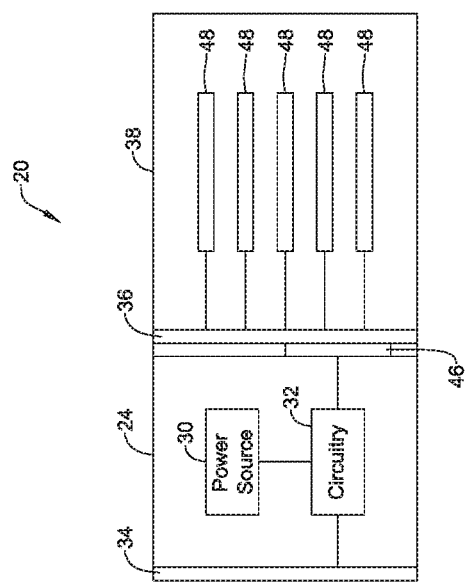
FIG. 5 is a schematic illustration of an IMD with one or more electrodes supported by an expandable anchoring member.

FIG. 5 is a schematic illustration of an IMD 20 with one or more electrodes 48 supported by the expandable anchoring member 38. In the example shown, the one or more electrodes 48 may each be supported by the expandable anchoring member 38. In some cases, one or more of the electrodes 48 may function as the cathode electrode of the IMD 20. In some cases, there may be a plurality of cathode electrodes. It is contemplated that two or more of the electrodes 48 may be connected in parallel to provide a distributed cathode electrode. Alternatively, it is contemplated that each of two or more of the electrodes 48 may be selectively connectable to the circuitry 32 by a switching circuit (part of circuitry 32), such that the circuitry 32 can use any one (or set) of the two or more electrodes 48 as the cathode electrode 36 at any given time. As shown in FIG. 5, the cathode electrode 36 may be part of and/or located on and/or supported by the expandable anchoring member 38. This may facilitate having the cathode electrode 36 engage a surface of a patient's heart (e.g., engage an atrium of the heart, which may include an atrial appendage).

The cathode electrode 36, when part of the expandable anchoring member 38 and/or at other times, may be in electrical communication with (e.g., operably coupled to) the circuitry 32 directly or via an interconnect 46. The interconnect 46 may be part of the hub 41, but this is not required. The interconnect 46 may be any electrically conductive trace or circuit acting as an intermediary between the cathode electrode 36 and the circuitry 32. In one example, the interconnect 46 may include an electrically conductive surface that engages an electrically conductive surface of the housing 22 and/or one or more elements extending from the housing 22 to mechanically engage and/or attach to the hub 41. The attachment or engagement of the housing 22 with the expandable anchoring member 38 may facilitate operatively coupling the interconnect 46 with circuitry 32.

One or more of the electrodes 48 may take any configuration on the expandable anchoring member 38. In one example, the one or more electrodes 48 may be a single electrode that may extend circumferentially around the expandable anchoring member 38 to sense electrical signals of a patient in which the IMD 20 is implanted and/or to utilize the electrode 48 for pacing the patient's heart. Alternatively, the one or more electrodes 48 may be located on a single lateral side of the expandable anchoring member 38 for sensing electrical signals of the patient's heart at a specific location and/or to pace the patient's heart at a specific location.

In another example, the one or more electrodes 48 of the expandable anchoring member 38 may include a plurality of circumferentially spaced electrodes 48 for sensing electrical signals of the patient's heart and/or for pacing the patient's heart. In some cases, the circuitry 32 of the IMD 20 may be configured to utilize one or more of the circumferentially spaced electrodes for sensing electrical signals of the patient's heart, make a determination as to the best locations to provide pacing signals along the circumference of the expandable anchoring member 38 based, at least in part, on the sensed electrical signals, and then initiate pacing at those specific locations according to a desired pacing width and pacing rate. In one example, the circuitry 32 may perform a capture threshold test and identify which one or more of the multiple spaced electrodes 48 has the lowest capture threshold(s), and may then use those electrodes during subsequent pacing of the RAA, RA, LAA or LA. The switching circuit discussed above may selectively connect each (or a set) of the electrodes 48 to the circuitry such that the circuitry 32 can use any one (or set) of the electrodes 48 as the cathode electrode 36 at any given time.

As discussed above, the expandable anchoring member 38 may include one or more expandable members 40. The expandable members 40 may take on one or more configurations. For example, the expandable members 40 may include struts, an expandable wire mesh, a coiled wired, a balloon, and/or any other suitable configuration that may expand from a collapsed configuration to an expanded configuration. In some cases, the expandable members 40 may extend generally along a longitudinal axis A (e.g., a central axis) from a first end 42 to a second end 44 of the expandable members 40 when in the collapsed configuration, but this is not required.

Figure 6A:
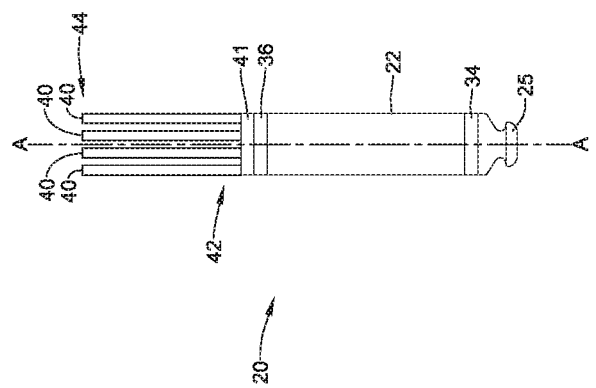
FIG. 6A is a schematic diagram of an illustrative IMD in a collapsed configuration.

The expandable members 40 may be circumferentially spaced from one another and in some cases, the expandable members 40 may extend from the hub 41 (e.g., a central hub), but this is not required. In some cases, the expandable members 40 may be located circumferentially about the longitudinal axis A, such as is shown in FIG. 6A. In a collapsed configuration, the expandable members 40 may, in some cases, extend parallel or substantially parallel to the longitudinal axis A from the first end 42 to the second end 44. In an expanded configuration, the second end 44 of the expandable members 40 and/or portions between the second end 44 and the first end 42 of the expandable members 40 may extend out or away from the longitudinal axis A. In some cases, the first end 42 of the expandable members 40 may be fixed with respect to the longitudinal axis A, sometimes via the hub 41.

Figure 6B:
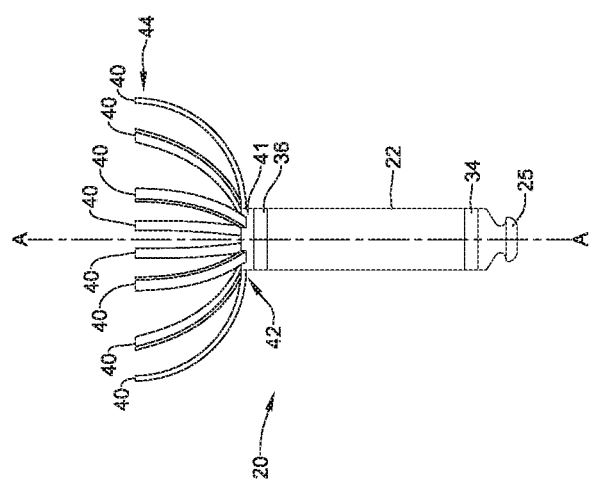
FIG. 6B is a schematic diagram of the illustrative IMD of FIG. 6A in an expanded configuration.
Figure 6C:
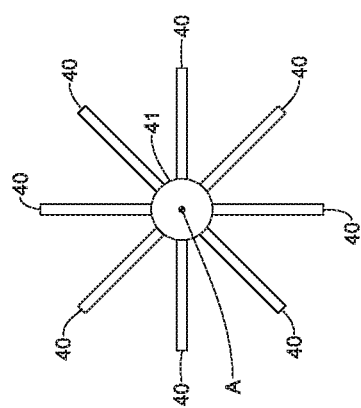
FIG. 6C is a schematic view of the illustrative IMD of FIG. 6B in the expanded configuration when viewed from the distal end.

As shown in FIGS. 6A-6C, in one example, the expandable members 40 of the expandable anchoring member 38 may be or may include a plurality of struts. The expandable members 40 in FIG. 6A may be connected to the hub 41, where the hub is connected to and/or is configured to be connected to the housing 22. FIG. 6A depicts the expandable members 40 in a collapsed configuration. FIG. 6B depicts the expandable members 40 in an expanded configuration forming a closed first end and an open second end (e.g., to form a cup-shape). FIG. 6C depicts the expandable members 40 in an expanded configuration when viewed from a distal end of the IMD 20.

The struts may include a first end interconnected with other struts via a hub (e.g., a central hub such as hub 41) or other feature, and a second end that is free from engagement with other structures. However, this is not required and both of the first end and the second end of the struts may be interconnected with other struts, hubs, or other features, or neither the first end nor the second end of the struts may be interconnected.

In some cases, the expandable members 40 are in strut form and may be formed from a monolithic piece of material. For example, the expandable members 40 may be made from a tube of nickel-titanium alloy (e.g., NITINOL), where the expandable members (e.g., struts) may be cut (e.g., laser cut or cut in another manner) and the material thereof may be heat worked such that the expandable members 40 may self-expand when in an unrestricted state (e.g. is pushed out the distal end of a delivery catheter). A first end of the tube may form a collar from which the expandable members 40 may extend to a second end of the tube. The collar may form the hub 41 or may be separate from the hub 41. In some cases, the collar may be affixed or otherwise attached to the hub 41.

Although the expandable members 40 and/or hub 41 may be made from a metal (e.g., NITINOL or one or more other suitable biocompatible metals), the expandable members 40 and/or hub 41 may be formed, at least in part, from one or more other biocompatible materials. In some cases, at least part of or all of the expandable members 40 and/or hub 41 may be formed from a polymer. In one example, the expandable members 40 and/or hub 41 may be formed, at least in part, from polytetrafluoroethylene (PTFE) and/or other polymer(s). More generally, it is contemplated that the expandable anchoring member 38 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In some cases, an expandable anchoring member such as the expandable anchoring member 38 may be formed of, coated with or otherwise include one or more polymeric materials. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

When the expandable members 40 include struts, there may be any number of struts forming the expandable anchoring member 38. In one example, the expandable anchoring member 38 may include at least one (1) strut, at least two (2) struts, at least five (5) struts, at least ten (10) struts, at least twenty (20) struts, at least forty (40) struts, and/or a greater number of struts. In a further example, there may be ten struts that extend from a first end (e.g., a collar), divide at a location approximately halfway between the first end and a second end of each strut into twenty struts, affix to a neighboring divided strut for a distance, and then the divided struts may rejoin to themselves to form ten second ends. The struts may be interconnected in any manner, including, but not limited to, via connectors, welding, brazing, soldering, braiding, and/or through one or more other connection techniques. In some cases, the struts may be cut from a single tube.

As shown in FIG. 6A, the struts forming the expandable members 40 are in the collapsed configuration, and are shown fixed to the hub 41, extending away from the housing 22 of the IMD 20, and extending substantially parallel to the longitudinal axis A from the first end 42 to the second end 44. As shown in FIG. 6B, the struts are shown in the expanded configuration, and extend away from the housing 22 of the IMD, extend toward the longitudinal axis A to the hub 41 at the first end 42, and extend out further from the longitudinal axis A at or near the second end 44.

Figure 7A:
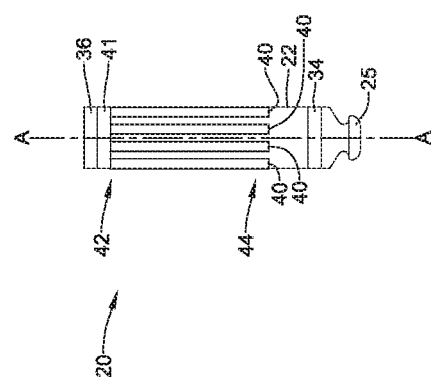
FIG. 7A is a schematic diagram of an illustrative IMD in a collapsed configuration.
Figure 12:
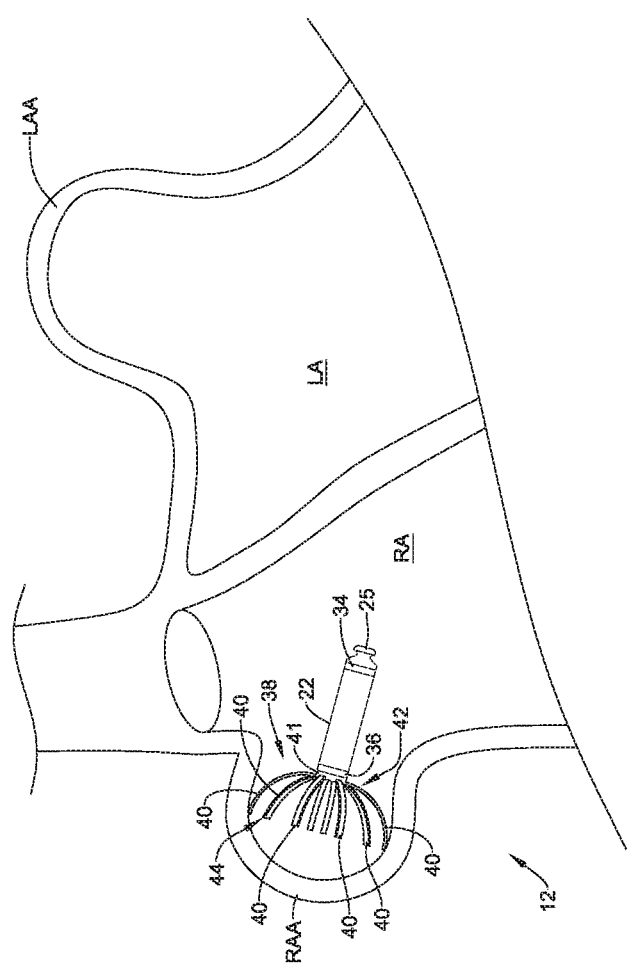
FIG. 12 is a schematic diagram of an illustrative IMD implanted within the right atrial appendage.

As shown in FIGS. 7A and 7B, in one example, the expandable members 40 (e.g., struts as shown in FIGS. 7A and 7B) of the expandable anchoring member 38 may be connected to the hub 41, where the hub 41 may be connected to and/or may be configured to be connected to the housing 22 such that the expandable members 40 may extend over the housing 22 of the IMD 20. FIG. 7A depicts the expandable members 40 in a collapsed configuration, extending proximally from the first end 42 of the expandable anchoring member 38 to the second end 44 of the expandable anchoring member 38 and over the housing 22 of the IMD 20, and extending substantially parallel to the longitudinal axis A from the first end 42 to the second end 44. In such configuration, the cathode electrode 36 may extend away from the expandable members 40 (e.g., the cathode electrode 36 may extend distal of the expandable members 40, as shown in FIG. 12 and discussed below). As shown in FIG. 7B, the expandable members 40 are in an expanded configuration forming a closed first end and an open second end (e.g., to form a cup-shape) with the expandable members 40 extending over the housing 22 of the IMD 20, extending toward the longitudinal axis A to the hub 41 at the first end 42, and extending out further from the longitudinal axis A at or near the second end 44.

In some cases, the expandable members 40 may extend away from the housing 22 of IMD 20 in the collapsed configuration, as shown for example in FIG. 6A, and then in the expanded configuration, extend over the housing 22 of the IMD 20, as shown for example in FIG. 7B. Further, in some cases, the expandable members 40 may extend over or adjacent the housing 22 of IMD 20 in the collapsed configuration, as shown for example in FIG. 7A, and then in the expanded configuration, extend away from the housing 22 of the IMD 20, as shown for example in FIG. 6B. Further, other configurations and combinations of collapsed and expanded configurations are contemplated, where the configurations and combinations of collapsed and expanded configurations facilitated delivery, implantation, and position maintenance of the implanted IMD 20.

In some cases, the expandable anchoring member 38 may be biased to the expanded configuration and expand away from the longitudinal axis A at the second end 44 when transitioning from the collapsed configuration to the expanded configuration. In some cases, a balloon catheter, a threaded expansion device, or other device may be used to manually drive the expandable anchoring member 38 to the expanded configuration.

While not required, at least some of the expandable members 40 may include one or more electrodes (e.g., electrodes 48, not shown in FIGS. 6A-7B). The electrodes of the expandable members 40 may be operatively coupled to the cathode electrode 36, sometimes through a switching circuit. Sometimes, the expandable members 40 are electrically isolated from one another, and each of the expandable members 40 may include an electrically conductive material and may have an exposed portion that forms an electrode 36, while maintaining mechanical properties to engage a patient's heart to fix the IMD 20 in place.

Figure 8:
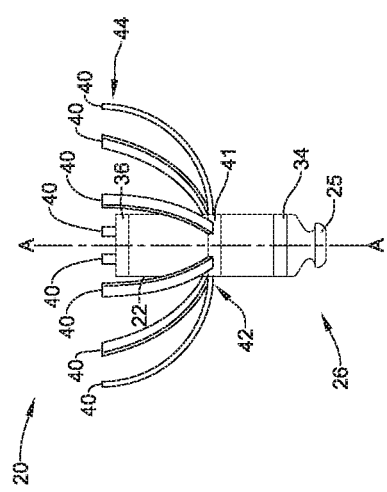
FIG. 8 is a schematic diagram of an illustrative IMD in an expanded configuration.
Figure 9:
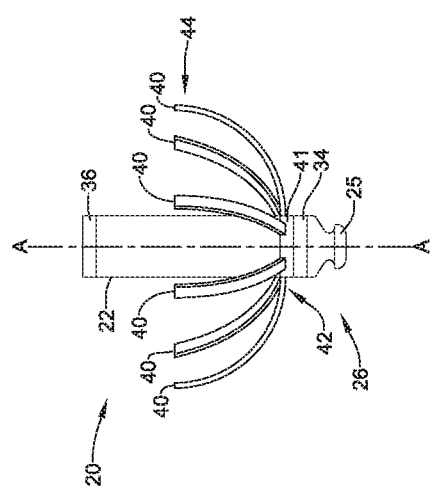
FIG. 9 is a schematic diagram of another illustrative IMD in an expanded configuration.

In some cases, the housing 22 may be secured (e.g., fixedly or releasably secured) to the expandable anchoring member 38 such that the housing 22 may extend from the first end 42 of the expandable anchoring member 38 toward the second end 44 of the expandable anchoring member 38. FIGS. 8 and 9 depict instances where at least part of the housing 22 extends from the first end 42 of the expandable anchoring member 38 toward the second end 44 of the expandable anchoring member 38.

In the IMDs 20 of FIGS. 8 and 9 and/or other cases, the housing 22 may engage the hub 41 and/or other portions of the expandable anchoring member 38, where at least part of the housing 22 may releasably engage the hub 41 or other portion of the expandable anchoring member 38 and/or at least part of the housing 22 may fixedly engage the housing 22 or other portion of the expandable member 38. The housing 22 may releasably engage the expandable anchoring member 38 with a releasable engagement including, but not limited to, a threaded engagement, a luer lock engagement, a ball-detent engagement, and/or any other releasable engagement. Alternatively or in addition, the housing 22 may fixedly engage the expandable anchoring member 38 through a welding technique, a brazing technique, a soldering technique, and/or any other technique for fixedly engaging two elements to one another. In one example of engaging the housing 22 with the expandable anchoring member 38, the housing 22 may threadably engage the hub 41 to allow for removal of the housing 22 from the expandable anchoring member 38 after implantation of the IMD 20. Alternatively or in addition, at least part of the housing 22 may fixedly engage the hub 41 and at least part of the IMD 20 may be releasable from the housing 22 (e.g., although not shown in FIGS. 8 and 9, the power source 30 may be releasable from the housing 22 as discussed above with respect to FIGS. 4A and 4B) and/or releasable from the expandable anchoring member 30.

FIG. 8 depicts the housing 22 (e.g., a housing having a shorter length than the housing 22 in FIG. 9, discussed below) than engaging the expandable anchoring member 38 and extending from the first end 42 of the expandable anchoring member 38 toward the second end 44 of the expandable anchoring member 38, where the first end 24 of the housing 22 does not extend beyond ends of the expandable members 40 at the second end 44 of the expandable anchoring member 38. When the first end 24 of the housing 22 does not extend past ends of the expandable members 40 with the expandable anchoring member 38 in an expanded configuration, the expandable members 40 may include electrodes (e.g., electrodes 48, as shown in FIG. 5) that may be in communication with the cathode electrode 36 of the housing 22 and/or that may perform sensing and/or pacing functions of a cathode electrode. Other electrodes in communication with the cathode electrode 36 and/or that may perform sensing and/or pacing functions of a cathode electrode may be utilized.

FIG. 9 depicts the housing 22 (e.g., an elongated housing as compared to the housing 22 of FIG. 8) engaging the expandable anchoring member 38 and extending from the first end 42 of the expandable anchoring member 38 toward the second end 44 of the expandable anchoring member 38, where the first end 24 of the housing 22 may extend beyond the second end 44 of the expandable anchoring member 38. When first end 24 of the housing 22 does extend past ends of the expandable members 40 with the expandable anchoring member 38 in an expanded configuration, the IMD 20 may be deployed and/or positioned such that the cathode electrode 36 may engage a heart wall to sense signals from the heart H and/or apply pace signals to the heart H and the expandable anchoring member 38 maintains the engagement between the cathode electrode 36 and the heart wall. Alternatively or in addition, the expandable members 40 may include other electrodes (e.g., electrodes 48, as shown in FIG. 5) that may be in communication with the cathode electrode 36 of the housing 22 and/or that may perform sensing and/or pacing functions of a cathode electrode. Other electrodes in communication with the cathode electrode 36 and/or that may perform sensing and/or pacing functions of a cathode electrode may be utilized.

Figure 10:
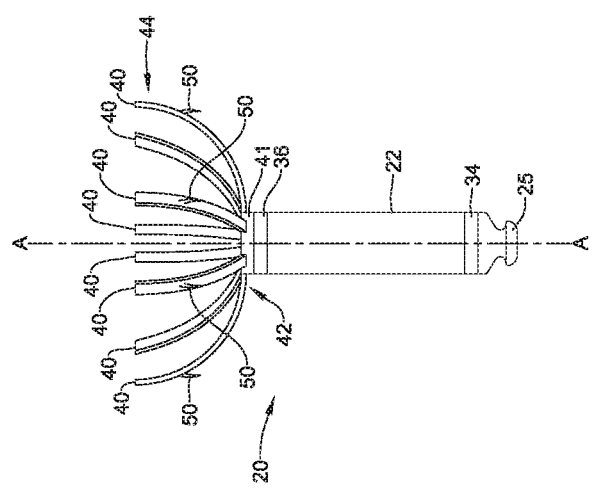
FIG. 10 is a schematic diagram of an illustrative IMD with fixation features extending from struts of an expandable anchoring member.

In some cases, the expandable anchoring member 38 may include one or more fixation features for engaging a patient's heart and to secure the expandable anchoring member 38 and the housing 22 to the patient's heart H. For example, and as shown in FIG. 10, a fixation feature 50 may be a tine, a wire, and/or other feature extending from the expandable members 40. Illustratively, one or more fixation features 50 may extend from each expandable member 40 such that the fixation features 50 may be circumferentially spaced around the expandable anchoring member 38 to engage the heart H at a plurality of spaced locations. The fixation features 50 may be configured to extend away from the longitudinal axis A, extend in a distal direction, and/or extend in a proximal direction to engage the patient's heart wall (e.g., walls of the RAA or walls of the RA) as the expandable members 40 radially expand from the central axis A-A during deployment of the IMD 20. In some cases, although the expandable members 40 radially expand to secure the IMD 20 at an implant location, the fixation features 50 may engage the wall of the RAA or other portion the heart to provide additional stabilization and/or prevent the IMD 20 from backing out of the RAA once it has been placed. The biased nature of the expandable members 40 may facilitate maintaining engagement between the fixation features 50 and the patient's heart H.

Figure 11:
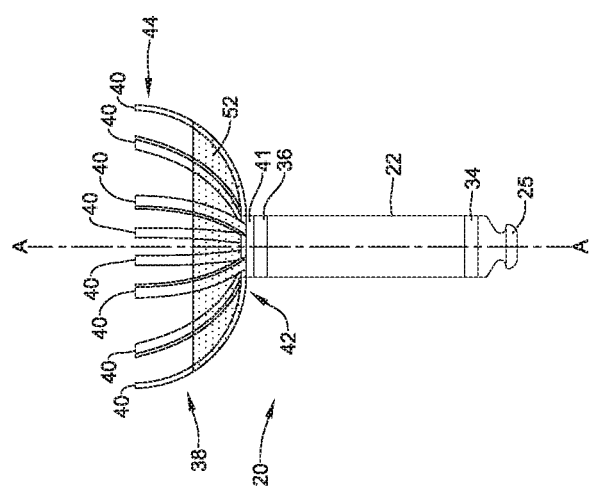
FIG. 11 is a schematic diagram of an illustrative IMD with a membrane supported by an expandable anchoring member.

FIG. 11 depicts the illustrative IMD 20 with the expandable anchoring member 38 in the expanded configuration. The IMD 20 in FIG. 11 includes a membrane 52 covering a portion of the expandable anchoring member 38. The membrane 52 may be applied to the expandable anchoring member 38 such that it covers at least a portion of the expandable members 40 and in some cases, an entire length from the first end 42 to the second end 44 of the expandable members 40. As shown in the example of FIG. 11, the membrane 52 may extend from first end 42 of the expandable members 40 toward the second end 44 of the expandable members 40, but may end prior to reaching the second end 44 of the expandable members 40. In one example, the membrane 52 may end at a location between one-third and two-thirds a distance from the first end 42 to the second end 44 of the expandable members 40. Further, the membrane 52 may cover at least part of an interior surface of the expandable members 40, at least part of an exterior surface of the expandable members 40, and/or at least part of an interior surface and an exterior surface of the expandable members 40. An exterior surface of the expandable members 40 may be a surface configured to interface with a wall of a patient's heart H and an interior surface may be a surface of the expandable members 40 not configured to interface with a wall of the patient's heart H.

The membrane 52 may be attached to (e.g., secured to) the expandable members 40 and/or hub 41 in any manner. In one example, the membrane 52 may be attached to the expandable members 40 and/or hub 41 by sewing the membrane 52 to the expandable members 40 and/or hub 41 with thread, by gluing the membrane 52 to the expandable members 40 and/or hub 41 with adhesive, by forming the expandable anchoring member 38 around the membrane 52, and/or through one or more other connection techniques capable of withstanding an environment within a patient's heart.

The membrane 52 may be formed of any material. In one example, the membrane 52 may be formed of a mesh material. In some cases, the material of the membrane 52 may encourage endothelial cell growth over and/or around at least part of the expandable anchoring member 38. The mesh material may be a metal, a polymer, a fabric, other material, and/or a combination thereof. Some example materials for the membrane 52 may include, but are not limited to, polyethylene terephthalate (PET), polyester, and polyvinyl alcohol. In one example, the membrane 52 may be a mesh membrane formed from a piece of PET knit material that may be heat set to form a concave shape (e.g., a cup-shape or other concave shape) that fits over the first end 42 of the expandable members 40.

FIG. 12 depicts the illustrative IMD 20 implanted in a patient's RAA. Although FIG. 12 may be described with respect to the IMD 20 being implanted in a patient's RAA, similar concepts may be utilized to implant the IMD 20 in a patient's LAA. As can be seen in FIG. 12, the expandable members 40 may extend distally from the first end 42 of the expandable anchoring member 38 to the second end 44 of the expandable anchoring member 38. The expandable members 40 may engage walls of the RAA to secure the IMD 20 in the heart H of the patient with the first end 42 of the expandable anchoring member 38 adjacent a proximal end of the RAA such that endothelial cell growth may cover a proximal end of the expandable anchoring member 38 and close off the RAA.

In some cases, the entire IMD 20 may be located in the RAA or, alternatively, at least a portion of the IMD 20 may extend out from the RAA and into the RA. In FIG. 12, the first end 42 of the expandable anchoring member 38 is shown secured to the housing 22, and the second end 44 of the expandable anchoring member 38 extends distally of the distal end of the housing 22 and into the RAA. Further, as can be seen in FIG. 12, the retrieval feature 25 may extend proximally from the housing 22 such that a retrieval device may be able to grasp or otherwise interact with the retrieval feature 25 to remove and/or adjust at least part of the IMD 20.

Figure 13:
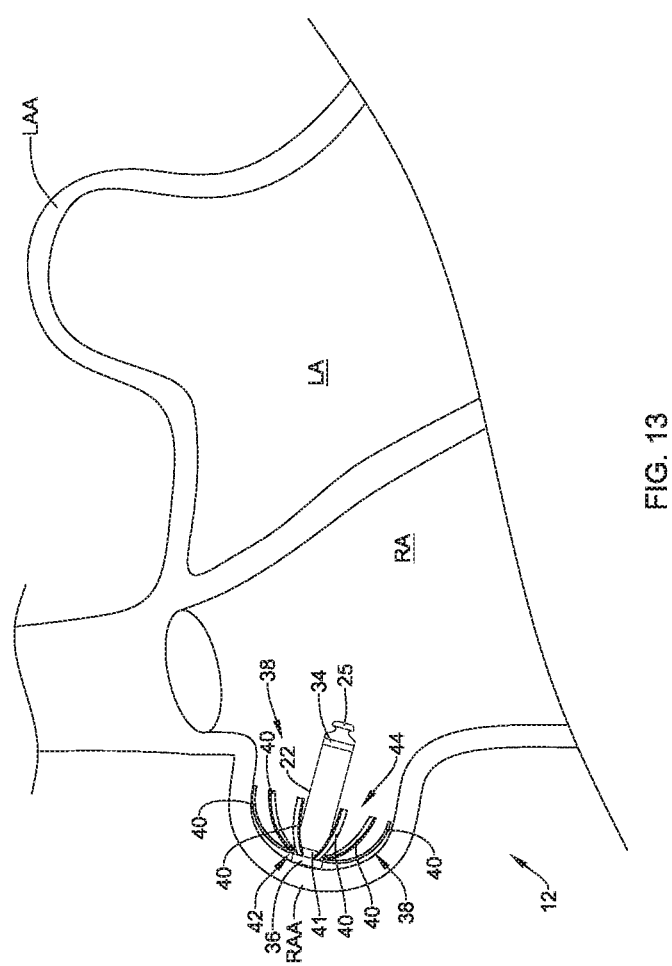
FIG. 13 is a schematic diagram of another illustrative IMD implanted within the right atrial appendage.

FIG. 13 depicts the illustrative IMD 20 implanted in a patient's RAA. Although FIG. 13 is described with respect to the IMD 20 being implanted in a patient's RAA, similar concepts may be utilized to implant the IMD 20 in a patient's LAA. As can be seen in FIG. 13, the expandable members 40 may extend proximally from the first end 42 of the expandable anchoring member 38 to the second end 44 of the expandable anchoring member 38. The expandable members 40 may engage walls of the RAA to secure the IMD 20 in the heart H of the patient and maintain a positioning of the cathode electrode 36 extending distally of the expandable members against the wall of the RAA. The first end 42 of the expandable anchoring member 38 is shown secured to the housing 22, and the second end 44 of the expandable anchoring member 38 extends proximally of the distal end of the housing 22. In some cases, the entire IMD 20 may be located in the RAA or, alternatively, at least a portion of the IMD 20 may extend out from the RAA and into the RA. As can be seen in FIG. 13, the retrieval feature 25 may extend proximally from the housing 22 such that a retrieval device may be able to grasp or otherwise interact with the retrieval feature 25 to remove and/or adjust at least part of the IMD 20.

Figure 14:
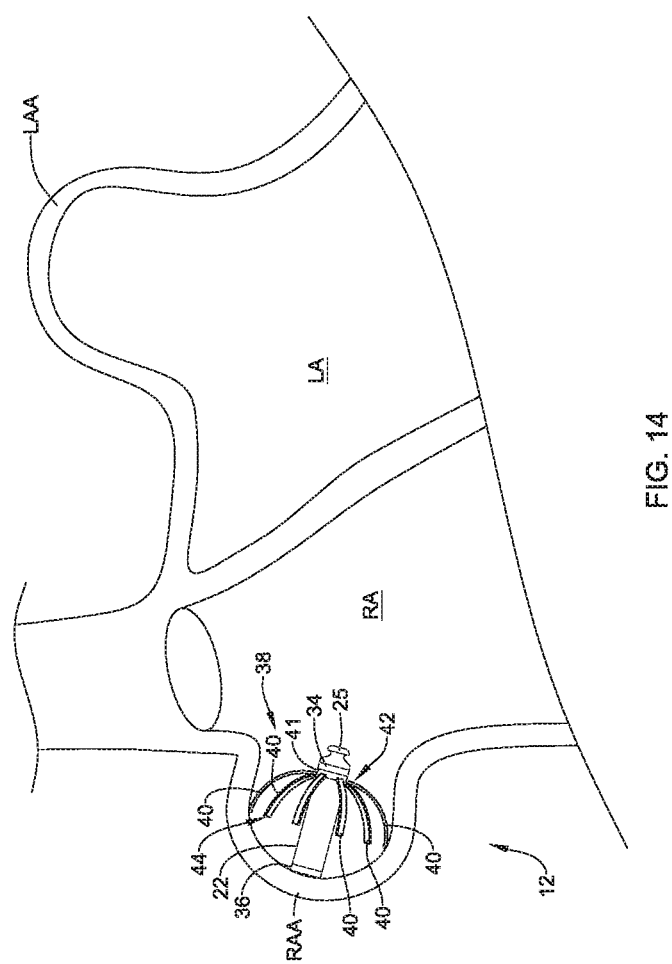
FIG. 14 is a schematic diagram of another illustrative IMD implanted within the right atrial appendage.

FIG. 14 depicts the illustrative IMD 20 implanted in a patient's RAA. Although FIG. 14 is described with respect to the IMD 20 being implanted in a patient's RAA, similar concepts may be utilized to implant the IMD 20 in a patients LAA. As can be seen in FIG. 14, the expandable members 40 may extend distally from the first end 42 of the expandable anchoring member 38 to the second end 44 of the expandable anchoring member 38. The expandable members 40 may engage walls of the RAA to secure the IMD 20 in the heart H of the patient with the first end 42 of the expandable anchoring member 38 adjacent a proximal end of the RAA such that endothelial cell growth may cover a proximal end of the expandable anchoring member 38 and close off the RAA.

In FIG. 14, the first end 42 of the expandable anchoring member 38 is shown secured to the housing 22, and the housing 22 may extend distally of ends of the expandable members 40 at the second end 44 of the expandable anchoring member 38, but this is not required (e.g., see FIG. 8). In such a configuration, however, when the IMD 20 is implanted, the cathode electrode 36 of the housing 22 may engage a wall of the RAA and the expandable anchoring member 38 may maintain engagement of the cathode electrode 36 with a wall of the RAA.

In some cases, the entire IMD 20 may be located in the RAA or, alternatively, at least a portion of the IMD 20 may extend out from the RAA and into the RA (e.g., see the IMD 20 configurations of FIGS. 8 and 9). Further, as can be seen in FIG. 14, at least the retrieval feature 25 may extend proximally from the housing 22 and/or the expandable anchoring mechanism 38 such that a retrieval device may be able to grasp or otherwise interact with the retrieval feature 25 to remove and/or adjust at least part of the IMD 20.

Figure 15:
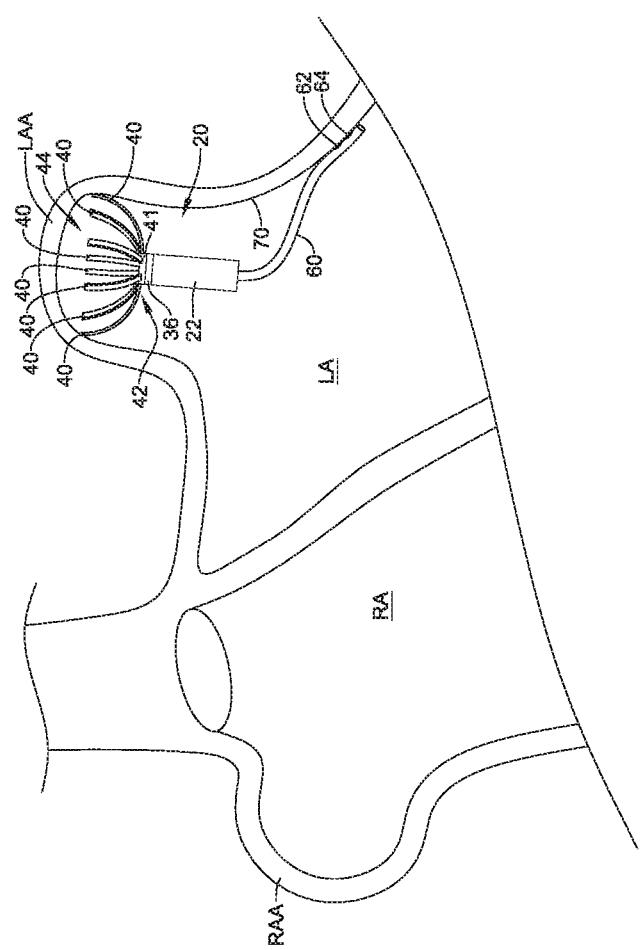
FIG. 15 is a schematic illustration of an IMD implanted within the left atrial appendage, with a lead structure extending into the left atrium.

FIG. 15 is a schematic diagram of the illustrative IMD 20 implanted within the LAA. Although FIG. 15 is described with respect to the IMD 20 being implanted in a patient's LAA, similar concepts may be utilized to implant the IMD 20 in a patients RAA. As can be seen in FIG. 14, an expandable members 40 may extend distally from the first end 42 of the expandable anchoring member 38 to the second end 44 of the expandable anchoring member 38. The expandable members 40 may engage walls of the LAA to secure the IMD 20 in the heart H of the patient. The first end 42 of the expandable anchoring member 38 is shown secured to the housing 22, and the second end 44 of the expandable anchoring member 38 is shown extending distally of the distal end of the housing 22. The illustrative IMD 20 in FIG. 15 may include a tail 60 extending from the second end of the housing 22 and into the LA.

In some cases, the tail 60 may be shaped to provide a bias force against a wall 70 of the LA. While the tail 60 is shown extending into the LA, it will be appreciated that in some cases, the tail 60 may be configured to extend into the LV, RA, and/or RV. In some cases, the tail 60 may be configured to extend into cardiac vasculature such as but not limited to the coronary sinus.

The tail 60 may include one or more electrodes, such as electrodes 62 and 64 and/or other electrodes. The electrodes 62 and 64 may be configured to engage a wall of the LA, as shown.

In some cases, the electrodes 62, 64 may be used in combination with the anode electrode 34 and a cathode electrode 36 for pacing within the LA or other portions of the heart H. In some cases, the electrodes 62, 64, and others if present on the tail, may be used in place of the anode electrode 34 and/or the cathode electrode 36 for pacing within the LA or other location in the heart H. In some cases, the cathode electrode 36 may be omitted, and one or more of the electrodes 62, 64 may be used as the cathode along with the anode electrode 34 to pace the atrium. In some cases, the electrodes 62, 64 may be used in combination with or in place of the anode electrode 34 and/or the cathode electrode 36 to sense electrical activity in and/or near the LA.

In some cases, multiple spaced electrodes 62, 64 may be provided along a length of the tail 60. Circuitry 32 within housing 22 may be configured to select a particular electrode from the multiple spaced electrodes 62, 64 for use as the cathode during subsequent pacing. In some cases, the circuitry 32 may perform a capture threshold test and identify which of the multiple spaced electrodes 62, 64 has the lowest capture threshold, and may then use that electrode during subsequent pacing of the LA. While the IMD 20 is shown implanted in the LAA, it is contemplated that it could likewise be implanted in the RAA and used to pace and/or sense in the RA.

Figure 16:
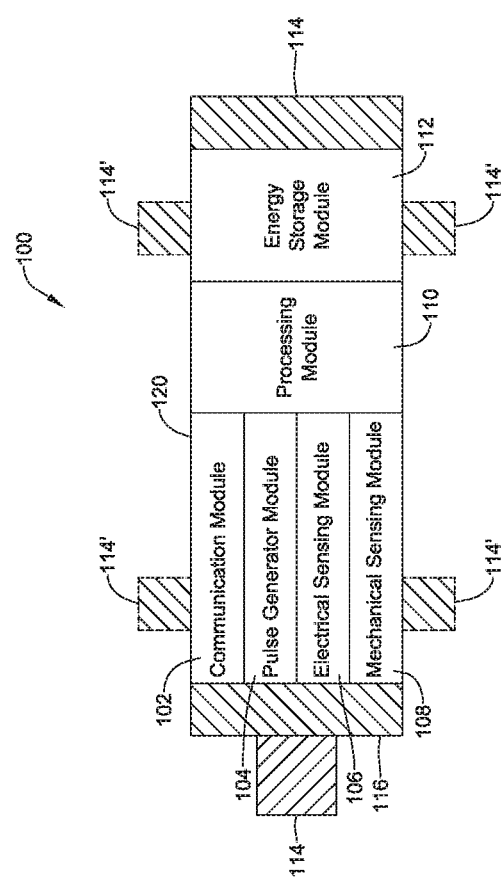
FIG. 16 is a schematic block diagram of an illustrative leadless cardiac pacemaker (LCP), which may be considered as being an example housing in the IMDs of FIGS. 2 through 15.

FIG. 16 is a schematic block diagram of an illustrative leadless cardiac pacemaker (LCP) 100, which may be considered as being an example housing in the IMDs of FIGS. 2 through 15. The LCP 100 may operate to sense physiological signals and parameters and deliver one or more types of electrical stimulation therapy to the heart of the patient. Example electrical stimulation therapy may include bradycardia pacing, rate responsive pacing therapy, cardiac resynchronization therapy (CRT), anti-tachycardia pacing (ATP) therapy and/or the like. As can be seen in FIG. 16, the LCP 100 may be a compact device with all components housed within the LCP 100 or directly on a housing 120. In some instances, the LCP 100 may include one or more of a communication module 102, a pulse generator module 104, an electrical sensing module 106, a mechanical sensing module 108, a processing module 110, an energy storage module 112, and electrodes 114.

As depicted in FIG. 16, the LCP 100 may include electrodes 114, which can be secured relative to the housing 120 and electrically exposed to tissue and/or blood surrounding the LCP 100. The electrodes 114 may represent the anode electrode 34, the cathode electrode 36 and/or electrodes 48 discussed above. The electrodes 114 may generally conduct electrical signals to and from the LCP 100 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by an electrocardiogram (ECG). The electrodes 114 may include one or more biocompatible conductive materials such as various metals or alloys that are known to be safe for implantation within a human body. In some instances, the electrodes 114 may be generally disposed on either end of the LCP 100 and may be in electrical communication with one or more of modules the 102, 104, 106, 108, and 110. In embodiments where the electrodes 114 are secured directly to the housing 120, an insulative material may electrically isolate the electrodes 114 from adjacent electrodes, the housing 120, and/or other parts of the LCP 100. In some instances, some or all of the electrodes 114 may be spaced from the housing 120 and may be connected to the housing 120 and/or other components of the LCP 100 through connecting wires, the expandable anchoring member 38, and/or other structure. In some cases, one or more of the electrodes 114 may be placed on a tail (see FIG. 15) that extends out away from the housing 120, such as out into the adjacent heart chamber.

As shown in FIG. 16, in some embodiments, the LCP 100 may include electrodes 114'. The electrodes 114' may be in addition to the electrodes 114, or may replace one or more of the electrodes 114. The electrodes 114' may be similar to the electrodes 114 except that the electrodes 114' are disposed on the sides of the LCP 100. In some cases, the electrodes 114' may increase the number of electrodes by which the LCP 100 may deliver communication signals and/or electrical stimulation pulses, and/or may sense intrinsic cardiac electrical signals, communication signals, and/or electrical stimulation pulses. While generically shown as being the same size, it will be appreciated that one of the electrodes 114' may, for example, be relatively larger in surface area to be used as a pacing anode electrode while another of the electrodes 114' may be relatively smaller in surface area to be used as a pacing cathode electrode.

The electrodes 114 and/or 114' may assume any of a variety of sizes and/or shapes, and may be spaced at any of a variety of spacings. For example, the electrodes 114 may have an outer diameter of two to twenty millimeters (mm). In other embodiments, the electrodes 114 and/or 114' may have a diameter of two, three, five, seven millimeters (mm), or any other suitable diameter, dimension and/or shape. Example lengths for the electrodes 114 and/or 114' may include, for example, one, three, five, ten millimeters (mm), or any other suitable length. As used herein, the length is a dimension of the electrodes 114 and/or 114' that extends away from the outer surface of the housing 120. In some cases, the housing includes a protrusion (not shown) that extends away from the side of the housing, where the protrusion carries the anode electrode (e.g. electrode 114 or 114'). The protrusion may help space the anode electrode away from the side of the housing and into engagement with the patient's vasculature. In some instances, at least some of the electrodes 114 and/or 114' may be spaced from one another by a distance of fifteen, twenty, thirty, forty, fifty millimeters (mm), or any other suitable spacing. The electrodes 114 and/or 114' of a single device may have different sizes with respect to each other, and the spacing and/or lengths of the electrodes on the device may or may not be uniform.

In the illustrative embodiment shown, the communication module 102 may be electrically coupled to the electrodes 114 and/or 114' and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. The communication module 102 may additionally be configured to sense for communication signals delivered by other devices, which may be located external or internal to the patient's body.

The communication module 102 may communicate to help accomplish one or more desired functions. Some example functions include delivering sensed data, using communicated data for determining occurrences of events such as arrhythmias, coordinating delivery of electrical stimulation therapy, and/or other functions. In some cases, the LCP 100 may use communication signals to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 100 and/or another device, such as a determined heart rate, timing of determined heartbeats, timing of other determined events, determinations of threshold crossings, expirations of monitored time periods, accelerometer signals, activity level parameters, blood-oxygen parameters, blood pressure parameters, heart sound parameters, and the like. In some cases, processed information may, for example, be provided by a chemical sensor or an optically interfaced sensor. Messages and/or commands may include instructions or the like directing another device to take action, notifications of imminent actions of the sending device, requests for reading from the receiving device, requests for writing data to the receiving device, information messages, and/or other messages commands.

In at least some embodiments, the communication module 102 (or the LCP 100) may further include switching circuitry to selectively connect one or more of the electrodes 114 and/or 114' to the communication module 102 in order to select which of the electrodes 114 and/or 114' that the communication module 102 delivers communication pulses with. It is contemplated that the communication module 102 may be communicating with other devices via conducted signals, radio frequency (RF) signals, optical signals, acoustic signals, inductive coupling, and/or any other suitable communication methodology. Where the communication module 102 generates electrical communication signals, the communication module 102 may include one or more capacitor elements and/or other charge storage devices to aid in generating and delivering communication signals. In the embodiment shown, the communication module 102 may use energy stored in the energy storage module 112 to generate the communication signals. In at least some examples, the communication module 102 may include a switching circuit that is connected to the energy storage module 112 and, with the switching circuitry, may connect the energy storage module 112 to one or more of the electrodes 114/114' to generate the communication signals.

As shown in FIG. 16, a pulse generator module 104 may be electrically connected to one or more of the electrodes 114 and/or 114'. The pulse generator module 104 may be configured to generate electrical stimulation pulses and deliver the electrical stimulation pulses to tissues of a patient via one or more of the electrodes 114 and/or 114' in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 104 may generate electrical stimulation pacing pulses for capturing the heart of the patient, i.e. causing the heart to contract in response to the delivered electrical stimulation pulse. In some of these cases, the LCP 100 may vary the rate at which the pulse generator module 104 generates the electrical stimulation pulses, for example in rate adaptive pacing. In other embodiments, the electrical stimulation pulses may include defibrillation/cardioversion pulses for shocking the heart out of fibrillation or into a normal heart rhythm. In yet other embodiments, the electrical stimulation pulses may include anti-tachycardia pacing (ATP) pulses. It should be understood that these are just some examples. When used to treat other ailments, the pulse generator module 104 may generate electrical stimulation pulses suitable for neurostimulation therapy or the like. The pulse generator module 104 may include one or more capacitor elements and/or other charge storage devices to aid in generating and delivering appropriate electrical stimulation pulses. In at least some embodiments, the pulse generator module 104 may use energy stored in the energy storage module 112 to generate the electrical stimulation pulses. In some particular embodiments, the pulse generator module 104 may include a switching circuit that is connected to the energy storage module 112 and may connect the energy storage module 112 to one or more of the electrodes 114/114' to generate electrical stimulation pulses.

The LCP 100 may further include an electrical sensing module 106 and a mechanical sensing module 108. The electrical sensing module 106 may be configured to sense intrinsic cardiac electrical signals conducted from the electrodes 114 and/or 114' to the electrical sensing module 106. For example, the electrical sensing module 106 may be electrically connected to one or more of the electrodes 114 and/or 114' and the electrical sensing module 106 may be configured to receive cardiac electrical signals conducted through the electrodes 114 and/or 114' via a sensor amplifier or the like. In some embodiments, the cardiac electrical signals may represent local information from the chamber in which the LCP 100 is implanted. For instance, if the LCP 100 is implanted within an atrium or atrial appendage of the heart, cardiac electrical signals sensed by the LCP 100 through the electrodes 114 and/or 114' may represent atrial cardiac electrical signals. The mechanical sensing module 108 may include, or be electrically connected to, various sensors, such as accelerometers, including multi-axis accelerometers such as two- or three-axis accelerometers, gyroscopes, including multi-axis gyroscopes such as two- or three-axis gyroscopes, blood pressure sensors, heart sound sensors, piezoelectric sensors, blood-oxygen sensors, and/or other sensors which measure one or more physiological parameters of the heart and/or patient. Mechanical sensing module 108, when present, may gather signals from the sensors indicative of the various physiological parameters. The electrical sensing module 106 and the mechanical sensing module 108 may both be connected to the processing module 110 and may provide signals representative of the sensed cardiac electrical signals and/or physiological signals to the processing module 110. Although described with respect to FIG. 16 as separate sensing modules, in some embodiments, the electrical sensing module 106 and the mechanical sensing module 108 may be combined into a single module. In at least some examples, the LCP 100 may only include one of the electrical sensing module 106 and the mechanical sensing module 108. In some cases, any combination of the processing module 110, the electrical sensing module 106, the mechanical sensing module 108, the communication module 102, the pulse generator module 104 and/or the energy storage module may be considered a controller of the LCP 100.

The processing module 110 may be configured to direct the operation of the LCP 100 and may, in some embodiments, be termed a controller. For example, the processing module 110 may be configured to receive cardiac electrical signals from the electrical sensing module 106 and/or physiological signals from the mechanical sensing module 108. Based on the received signals, the processing module 110 may determine, for example, occurrences and types of arrhythmias and other determinations such as whether the LCP 100 has become dislodged. The processing module 110 may further receive information from the communication module 102. In some embodiments, the processing module 110 may additionally use such received information to determine occurrences and types of arrhythmias and/or and other determinations such as whether the LCP 100 has become dislodged. In still some additional embodiments, the LCP 100 may use the received information instead of the signals received from the electrical sensing module 106 and/or the mechanical sensing module 108—for instance if the received information is deemed to be more accurate than the signals received from the electrical sensing module 106 and/or the mechanical sensing module 108 or if the electrical sensing module 106 and/or the mechanical sensing module 108 have been disabled or omitted from the LCP 100.

After determining an occurrence of an arrhythmia, the processing module 110 may control the pulse generator module 104 to generate electrical stimulation pulses in accordance with one or more electrical stimulation therapies to treat the determined arrhythmia. For example, the processing module 110 may control the pulse generator module 104 to generate pacing pulses with varying parameters and in different sequences to effectuate one or more electrical stimulation therapies. As one example, in controlling the pulse generator module 104 to deliver bradycardia pacing therapy, the processing module 110 may control the pulse generator module 104 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For instance, the processing module 110 may monitor one or more physiological parameters of the patient which may indicate a need for an increased heart rate (e.g. due to increased metabolic demand). The processing module 110 may then increase the rate at which the pulse generator module 104 generates electrical stimulation pulses. Adjusting the rate of delivery of the electrical stimulation pulses may increase a comfort level of the patient by more closely matching the rate of delivery of electrical stimulation pulses with the cardiac output need of the patient.

For ATP therapy, the processing module 110 may control the pulse generator module 104 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, the processing module 110 may control the pulse generator module 104 to reduce the rate of delivered pacing pulses down to a safer level. In CRT, the processing module 110 may control the pulse generator module 104 to deliver pacing pulses in coordination with another device to cause the heart to contract more efficiently. In cases where the pulse generator module 104 is capable of generating defibrillation and/or cardioversion pulses for defibrillation/cardioversion therapy, the processing module 110 may control the pulse generator module 104 to generate such defibrillation and/or cardioversion pulses. In some cases, the processing module 110 may control the pulse generator module 104 to generate electrical stimulation pulses to provide electrical stimulation therapies different than those examples described above.

Aside from controlling the pulse generator module 104 to generate different types of electrical stimulation pulses and in different sequences, in some embodiments, the processing module 110 may also control the pulse generator module 104 to generate the various electrical stimulation pulses with varying pulse parameters. For example, each electrical stimulation pulse may have a pulse width and a pulse amplitude. The processing module 110 may control the pulse generator module 104 to generate the various electrical stimulation pulses with specific pulse widths and pulse amplitudes. For example, the processing module 110 may cause the pulse generator module 104 to adjust the pulse width and/or the pulse amplitude of electrical stimulation pulses if the electrical stimulation pulses are not effectively capturing the heart. Such control of the specific parameters of the various electrical stimulation pulses may help the LCP 100 provide more effective delivery of electrical stimulation therapy.

In some embodiments, the processing module 110 may further control the communication module 102 to send information to other devices. For example, the processing module 110 may control the communication module 102 to generate one or more communication signals for communicating with other devices of a system of devices. For instance, the processing module 110 may control the communication module 102 to generate communication signals in particular pulse sequences, where the specific sequences convey different information. The communication module 102 may also receive communication signals for potential action by the processing module 110.

In further embodiments, the processing module 110 may control switching circuitry by which the communication module 102 and the pulse generator module 104 deliver communication signals and/or electrical stimulation pulses to tissue of the patient. As described above, both the communication module 102 and the pulse generator module 104 may include circuitry for connecting one or more of the electrodes 114 and/or 114' (which may correspond to electrodes 34, 36, 48, 62, 64) to the communication module 102 and/or the pulse generator module 104 so those modules may deliver the communication signals and electrical stimulation pulses to tissue of the patient. The specific combination of one or more electrodes by which the communication module 102 and/or the pulse generator module 104 deliver communication signals and electrical stimulation pulses may influence the reception of communication signals and/or the effectiveness of electrical stimulation pulses. Although it was described that each of the communication module 102 and the pulse generator module 104 may include switching circuitry, in some embodiments, the LCP 100 may have a single switching module connected to the communication module 102, the pulse generator module 104, and the electrodes 114 and/or 114'. In such embodiments, processing module 110 may control the switching module to connect the modules 102/104 and the electrodes 114/114' as appropriate.

In some embodiments, the processing module 110 may include a pre-programmed chip, such as a very-large-scale integration (VLSI) chip or an application specific integrated circuit (ASIC). In such embodiments, the chip may be pre-programmed with control logic in order to control the operation of the LCP 100. By using a pre-programmed chip, the processing module 110 may use less power than other programmable circuits while able to maintain basic functionality, thereby potentially increasing the battery life of the LCP 100. In other instances, the processing module 110 may include a programmable microprocessor or the like. Such a programmable microprocessor may allow a user to adjust the control logic of the LCP 100 after manufacture, thereby allowing for greater flexibility of the LCP 100 than when using a pre-programmed chip. In still other embodiments, the processing module 110 may not be a single component. For example, the processing module 110 may include multiple components positioned at disparate locations within the LCP 100 in order to perform the various described functions. For example, certain functions may be performed in one component of the processing module 110, while other functions are performed in a separate component of the processing module 110.

The processing module 110, in additional embodiments, may include a memory circuit and the processing module 110 may store information on and read information from the memory circuit. In other embodiments, the LCP 100 may include a separate memory circuit (not shown) that is in communication with the processing module 110, such that the processing module 110 may read and write information to and from the separate memory circuit. The memory circuit, whether part of the processing module 110 or separate from the processing module 110, may be volatile memory, non-volatile memory, or a combination of volatile memory and non-volatile memory.

The energy storage module 112 may provide a power source to the LCP 100 for its operations. In some embodiments, the energy storage module 112 may be a non-rechargeable lithium-based battery. In other embodiments, the non-rechargeable battery may be made from other suitable materials. In some embodiments, the energy storage module 112 may be considered to be a rechargeable power supply, such as but not limited to, a rechargeable battery. In still other embodiments, the energy storage module 112 may include other types of energy storage devices such as capacitors or super capacitors. In some cases, as will be discussed, the energy storage module 112 may include a rechargeable primary battery and a non-rechargeable secondary battery. In some cases, the primary battery and the second battery, if present, may both be rechargeable. The LCP 100 may be coupled to an expandable anchoring member, such as the expandable anchoring member 38.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. A leadless cardiac pacemaker (LCP), the LCP comprising:
   a power source;
   circuitry operatively coupled to the power source, the circuitry configured to pace a patient's heart and/or sense electrical activity of the patient's heart;
   a housing at least partially enclosing the circuitry and configured to be positioned within an atrium of the patient's heart;
   an anode electrode operatively coupled to the circuitry;
   a cathode electrode operatively coupled to the circuitry, the cathode electrode spaced from the anode electrode; and
   an expandable anchoring member secured relative to the housing, the expandable anchoring member having a plurality of struts connected to a central hub at a first end and extend out to an open second end and having a collapsed configuration for delivery and an expanded configuration for securing the expandable anchoring member and the housing within the atrium of the patient's heart, with the cathode electrode in engagement with an atrium wall of the patient's heart; and
   a mesh contacting two or more of the plurality of struts of the expandable anchoring member and extending from the first end toward the second end, wherein the mesh is configured to encourage endotheliazation over at least part of the expandable anchoring member.

2. The LCP of claim 1, wherein the expandable anchoring member is configured to engage an atrial appendage of the patient's heart in the expanded configuration.

3. The LCP of claim 1, wherein the housing is secured to the central hub.

4. The LCP of claim 1, wherein in the collapsed configuration the plurality of struts of the expandable anchoring member extend substantially parallel to a central axis from the first end to the second end, and wherein in the expanded configuration the plurality of struts extend toward the central axis to the central hub at the first end and out further from the central axis at the second end.

5. The LCP of claim 4, wherein the plurality of struts are biased to expand away from the central axis at the second end when transitioning from the collapsed configuration to the expanded configuration.

6. The LCP of claim 4, further comprising a plurality of fixation features extending from one or more of the plurality of struts facing away from the central axis for engaging the patient's heart and to help secure the expandable anchoring member and the housing to the patient's heart.

7. The LCP of claim 6, wherein the plurality of fixation features are configured to engage an atrial appendage of the patient's heart as the plurality of struts radially expand from the central axis at the second end of the expandable anchoring member.

8. The LCP of claim 7, wherein the plurality of struts are biased to keep the plurality of fixation features engaged with the patient's heart when the expandable anchoring member is in the expanded configuration.

9. The LCP of claim 1, wherein the housing is removably secured to the expandable anchoring member.

10. The LCP of claim 1, wherein the power source is removably coupled relative to the housing, and is removable relative to the housing while the housing remains secured to the expandable anchoring member.

11. The LCP of claim 1, wherein the expandable anchoring member comprises the cathode electrode and further comprises an interconnect for providing a connection to the cathode electrode, and wherein the circuitry is operatively coupled to the interconnect and thus the cathode electrode.

12. The LCP of claim 11, wherein the cathode electrode is part of or supported by at least one of the plurality of struts.

13. The LCP of claim 1, wherein the expandable anchoring member comprises a plurality of circumferentially spaced electrodes configured to engage the atrium of the patient's heart, wherein the plurality of circumferentially spaced electrodes are operatively coupled to the circuitry.

14. The LCP of claim 13, wherein the circuitry is configured to utilize one or more of the circumferentially spaced electrodes for sensing electrical signals of the patient's heart and/or to utilize one or more of the circumferentially spaced electrodes for pacing the patient's heart.

15. An implantable medical device (IMD), comprising:
    a power source;
    circuitry operatively coupled to the power source, the circuitry configured to pace a patient's heart and/or sense electrical activity of the patient's heart;
    a housing at least partially enclosing the circuitry and configured to be positioned within an atrium of the patient's heart;
    an anode electrode operatively coupled to the circuitry;
    a cathode electrode operatively coupled to the circuitry, the cathode electrode spaced from the anode electrode;
    an expandable anchoring member secured relative to the housing, the expandable anchoring member having a collapsed configuration for delivery and an expanded configuration for engaging an atrial wall of the patient's heart to secure the housing within the atrium of the patient's heart;
    wherein the expandable anchoring member extends from a first end to an open second end, wherein the open second end is configured to face the atrial wall, the expandable anchoring member further includes a plurality of struts connected to a central hub at the first end and extend out to the open second end; and
    a mesh contacting two or more of the plurality of struts of the expandable anchoring member and extending from the first end toward the second end, wherein the mesh is configured to encourage endotheliazation over at least part of the expandable anchoring member.

16. The IMD of claim 15, wherein the housing is secured to the central hub.

17. The IMD of claim 16, wherein at least part of the housing is releasably fixed to the expandable anchoring member.

18. An implantable medical device (IMD), comprising:
    a housing configured to be positioned within an atrium of a patient's heart;
    an anode electrode fixed relative to the housing;
    a cathode electrode fixed relative to the housing, the cathode electrode spaced from the anode electrode;
    an expandable anchoring member secured relative to the housing, the expandable anchoring member having a collapsed configuration for delivery and an expanded configuration for securing the expandable anchoring member and the housing within the atrium of the patient's heart;

the expandable anchoring member comprises four or more struts that, in the expanded configuration, assume an open ended cup shape; and a mesh contacting a plurality of the four or more struts of the expandable anchoring member and extending from the first end toward the second end, wherein the mesh is configured to encourage endotheliazation over at least part of the expandable anchoring member.

* * * * *